United States Patent

Peyman et al.

(10) Patent No.: US 6,723,727 B1
(45) Date of Patent: Apr. 20, 2004

(54) SUBSTITUTED PURINE DERIVATIVES, PROCESSES FOR THEIR PREPARATION, THEIR USE, AND COMPOSITIONS COMPRISING THEM

(75) Inventors: Anuschirwan Peyman, Kelkheim (DE); Jochen Knolle, Kriftel (DE); Volkmar Wehner, Sandberg (DE); Gerhard Breipohl, Frankfurt (DE); Jean-Francois Gourvest, Claye Souilly (FR); Denis Carniato, Marcoussis (FR); Thomas Richard Gadek, Oakland, CA (US)

(73) Assignees: Hoechst Aktiengesellschaft, Frankfurt am Main (DE); Genentech, South San Francisco, CA (US)

( * ) Notice: Subject to any disclaimer, the term of this patent is extended or adjusted under 35 U.S.C. 154(b) by 108 days.

(21) Appl. No.: 09/594,033

(22) Filed: Jun. 15, 2000

Related U.S. Application Data

(63) Continuation of application No. 08/996,475, filed on Dec. 22, 1997, now abandoned.

(30) Foreign Application Priority Data

Dec. 20, 1996 (DE) .......................................... 196 53 646

(51) Int. Cl.$^7$ .................... C07D 473/34; C07D 473/40; A61K 31/52; A61P 19/10; A61P 35/00
(52) U.S. Cl. .................. 514/263.21; 544/198; 544/207; 544/209; 544/264; 544/265; 544/266; 544/267; 544/268; 544/269; 544/270; 544/271; 544/272; 544/276; 544/277; 514/263.22
(58) Field of Search ................................ 514/261, 262, 514/263, 264, 265, 266, 267, 268, 269, 270, 271, 272, 276, 277, 263.2, 263.21, 263.22, 263.33, 263.35, 263.37, 263.38, 245

(56) References Cited

U.S. PATENT DOCUMENTS

| | | | | |
|---|---|---|---|---|
| 3,965,119 A | * | 6/1976 | Amann et al. | 540/596 |
| 3,984,555 A | * | 10/1976 | Amschler et al. | 514/252.17 |
| 4,075,409 A | * | 2/1978 | Greve et al. | 560/21 |
| 4,230,619 A | * | 10/1980 | Foglio et al. | 540/200 |
| 5,831,092 A | * | 11/1998 | Izawa et al. | 544/244 |
| 6,252,075 B1 | * | 6/2001 | Shiragami et al. | 544/276 |

FOREIGN PATENT DOCUMENTS

WO    WO 96/00574   *   1/1996

OTHER PUBLICATIONS

Byzova, Thromb Haemostat 80, 726 (1998).*
Samanen, Current Pharm. Design 3, 545 (1997).*
Hillis, Clinical Science 91, 639 (1996).*
Brooks, DN&P 10, 456 (1997).*
Engleman, Annual Rep Med Chem 31, 191 (1996).*
Storgard, J. Clinical Investigation 103, 47 (1999).*
Yun, Cancer Res. 56, 3103 (1996).*
Mousa, DDT, vol. 2, 187 (1997).*
Carron, Cancer Res. 58, 1930 (1998).*
Academic Press Dictionary of Science and Technology definition for "alkyl" from http://www.harcourt.com/dictionary/def/3/73/6/7/376700.html.*
IUPAC Acyclic Hydrocarbons Rules A–1.2 and A–3.5.*
Encarta® World English Dictionary definition for alkyl at http://dictionary.msn.com/find/print.asp?refid=1861584705&search=alkyl&wwi=2464.*
Hackh's Chemical Dictionary, 3rd edition p. 33 (1944).*
Hawley's Condensed Chemical Dictionary, 13th edition (1977) p. 34.*
Papadaki, Haema 1999; 2(4):180–191.*
Albelda, LAb. Investigation 68, 4, 1993.*
Bosman, Histochemical Journal 25, 469, 1993.*
Hall, J. Immunology 153:3218, 1994.*
Brown, Cardivascular research 28: 1815, 1994.*
Hammes, Abstract for Nat. Medcime 2, 529 (1996).*
Cox, DN&P 8, 197 (1995).*
http://cancerweb.ncl.ac.uk/cgi-bin/omod?query=alkyl&action=Search+OMD downloaded from the Internet Sep. 4, 2002.*
Kolata, "Two Drugs Eradicate Tumors in Mice" New York Times May 3, 1998, http://www.shamema.com/cancer-c.htm downloaded from the Internet Mar. 28, 2003.*
Marshall, "Setbacks for Endostatin" Science 295, 2198–2199 (Feb. 2002).*

(List continued on next page.)

Primary Examiner—Mark L. Berch
(74) Attorney, Agent, or Firm—Foley & Lardner

(57) ABSTRACT

The present invention relates to compounds of the formulae I and Ia

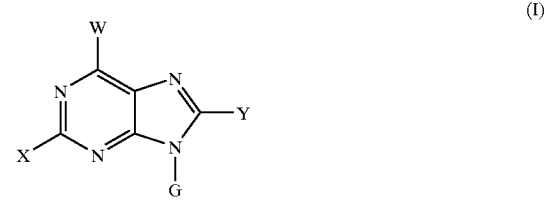

(I)

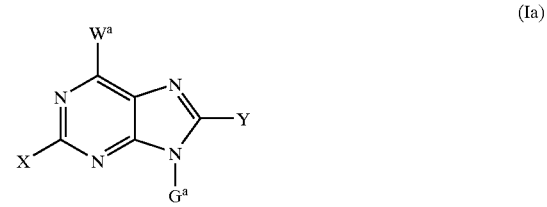

(Ia)

in which X, Y, W, $W^a$, G and $G^a$ have the meanings given in the patent claims, and their physiologically tolerable salts and their prodrugs, their preparation, their use, in particular as pharmaceutical active compounds, and pharmaceutical preparations comprising them. The compounds of the formula I are vitronectin receptor antagonists and can be employed, for example, as inhibitors of bone resorption and for the treatment of osteoporosis.

6 Claims, No Drawings

OTHER PUBLICATIONS

"Learning from Angiogenesis Trial Failures" http://www.genomics.org.cn:8080/bgi/english/news/englishnews%20020320-4.htm downloaded from the Internet Mar. 26, 2003.*

Sweeney et al, Trends in Molecular Medicine vol. 9(1), Jan. 2003, pp. 24-29.*

Benjamin K. Gill, "Diagram Representing the Roles of Cytokines in Inflammatory Responses" http://attila.stevens-tech.edu/chembio/bgill/IL10K.html downloaded from the Internet Aug. 12, 2002.*

Henry et al. Mini Rev Med Chem 2002 Dec. 2:531-42.*

Mousa, Current Opinion in Chemical Biology 6 (4), Aug. 1, 2002, pp. 534-541.*

* cited by examiner

SUBSTITUTED PURINE DERIVATIVES, PROCESSES FOR THEIR PREPARATION, THEIR USE, AND COMPOSITIONS COMPRISING THEM

This is a continuation of 08/996,475 filed Dec. 22, 1997, abandoned

The present invention relates to compounds of the formulae I and Ia

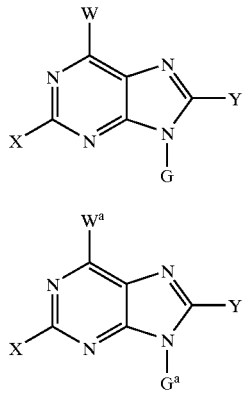

in which X, Y, W, $W^a$, G and $G^a$ have the meanings indicated below, and to their physiologically tolerable salts and their prodrugs, their preparation, their use and pharmaceutical preparations comprising them.

The compounds of the formula I are valuable pharmaceutical active compounds. In particular, they are vitronectin receptor antagonists and are suitable for the therapy and prophylaxis of illnesses which are based on the interaction between vitronectin receptors and their ligands in cell-cell or cell-matrix interaction processes or which can be prevented, alleviated or cured by influencing this interaction. The invention relates, inter alia, to the use of compounds of the formula I and of their physiologically tolerable salts and of pharmaceutical preparations which contain such compounds, as therapeutics for the prevention, alleviation or cure of illnesses which are caused at least partially by an undesired extent of bone resorption, angiogenesis or proliferation of cells of the vascular smooth musculature, or for whose therapy or prophylaxis an influencing of these processes is intended. In particular, the compounds of the formula I are suitable, for example, as inhibitors of bone resorption, as inhibitors of tumor growth and tumor metastasis, as antiinflammatories, for the treatment or prophylaxis of cardiovascular disorders, such as, for example, arteriosclerosis or restenosis, or for the treatment or prophylaxis of nephropathies and retinopathies, such as, for example, diabetic retinopathy.

The compounds of the formulae I and Ia according to the invention inhibit bone resorption by osteoclasts. Bone diseases against which the compounds of the formula I can be employed are especially osteoporosis, hypercalcemia, osteopenia, for example caused by metastases, dental disorders, hyperparathyroidism, periarticular erosions in rheumatoid arthritis and Paget's disease. The compounds of the formula I can furthermore be employed for the alleviation, avoidance or therapy of bone disorders which are caused by glucocorticoid, steroid or corticosteroid therapy or by a lack of sex hormone(s). All these disorders are characterized by bone loss which is based on the inequilibrium between bone formation and bone destruction.

Human bones are subject to a constant dynamic renovation process comprising bone resorption and bone formation. These processes are controlled by types of cell specialized for these purposes. Bone formation is based on the deposition of bone matrix by osteoblasts, and bone resorption is based on the destruction of bone matrix by osteoclasts. The majority of bone disorders are based on a disturbed equilibrium between bone formation and bone resorption. Osteoporosis is characterized by a loss of bone matrix. Activated osteoclasts are polynuclear cells having a diameter of up to 400 μm, which remove bone matrix. Activated osteoclasts become attached to the surface of the bone matrix and secrete proteolytic enzymes and acids into the so-called "sealing zone", the region between their cell membrane and the bone matrix. The acidic environment and the proteases cause the destruction of the bone.

Studies have shown that the attachment of osteoclasts to the bones is controlled by integrin receptors on the cell surface of osteoclasts. Integrins are a superfamily of receptors which include, inter alia, the fibrinogen receptor $a_{IIb}\beta_3$ on the blood platelets and the vitronectin receptor $a_v\beta_3$. The vitronectin receptor $a_v\beta_3$ is a membrane glycoprotein which is expressed on the cell surface of a number of cells such as endothelial cells, cells of the vascular smooth musculature, osteoclasts and tumor cells. The vitronectin receptor $a_v\beta_3$, which is expressed on the osteoclast membrane, controls the process of attachment to the bone and bone resorption and thus contributes to osteoporosis, $a_v\beta_3$ in this case binds to bone matrix proteins such as osteopontin, bone sialoprotein and thrombospontin, which contain the tripeptide motif Arg-Gly-Asp (or RGD).

Horton and co-workers describe RGD peptides and an anti-vitronectin receptor. antibody (23C6) which inhibit tooth destruction by osteoclasts and the migration of osteoclasts (Horton et al., Exp. Cell. Res. 1991, 195, 368). In J. Cell Biol. 1990, 111, 1713, Sato et al. describe echistatin, an RGD peptide from snake venom, as a potent inhibitor of bone resorption in a tissue culture and as an inhibitor of osteoclast adhesion to the bone. Fischer et al. (Endocrinology 1993, 132, 1411) were able to show in the rat that echistatin also inhibits bone resorption in vivo. Wayne et al. (J. Clin. Invest. 1997, 99, 2284) were able to demonstrate in the rat the in vivo efficacy of the inhibition of bone resorption by a vitronectin receptor antagonist.

The vitronectin receptor $a_v\beta_3$ on human cells of the vascular smooth musculature of the aorta stimulates the migration of these cells into the neointima, which finally leads to arteriosclerosis and restenosis after angioplasty (Brown et al., Cardiovascular Res. 1994, 28, 1815).

Brooks et al. (Cell 1994, 79, 1157; J. Clin. Invest. 96 (1995) 1815) and Mitjans et al., J. Cell Science 1995, 108, 2825) showed that antibodies against $a_v\beta_3$ or $a_v\beta_3$ antagonists can cause a shrinkage of tumors by inducing the apoptosis of blood vessel cells during angiogenesis. Cheresh et al. (Science 1995, 270, 1500) describe anti-$a_v\beta_3$ antibodies or $a_v\beta_3$ antagonists which inhibit the bFGF-induced angiogenesis process in the rat eye, a property which can be used therapeutically in the treatment of retinopathies.

EP-A-0 528 586 and EP-A-0 528 587 disclose aminoalkyl- or heterocyclyl-substituted phenylalanine derivatives, and WO 95/32710 discloses aryl derivatives as inhibitors of bone resorption by osteoclasts. WO 95/28426 describes RGD peptides as inhibitors of bone resorption, angiogenesis and restenosis. WO 96/00574 and WO 96/26190 describe benzodiazepines, inter alia, as vitronectin receptor antagonists or integrin receptor antagonists. WO 96/00730 describes fibrinogen receptor antagonist templates, in particular benzodiazepines, which are linked to a nitrogen-bearing 5-membered ring, as vitronectin receptor antagonists. EP-A0 531 883 describes fused 5-membered heterocycles which inhibit fibrinogen binding to platelets.

The present invention relates to compounds of the formulae I and Ia

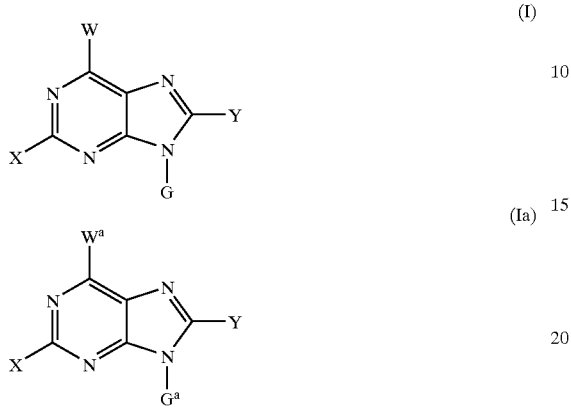

in which:

X is hydrogen, $NR^6R^{6'}$, fluorine, chlorine, bromine, $OR^6$, $SR^6$, hydroxy-$(C_1-C_6)$-alkyl-NH, (hydroxy-$(C_1-C_6)$-alkyl)$_2$N, amino-$(C_1-C_6)$-alkyl-NH, (amino-$(C_1-C_6)$-alkyl)$_2$N, hydroxy-$(C_1-C_6)$-alkyl-O, hydroxy-$(C_1-C_6)$-alkyl-S or NH—CO—$R^6$;

Y is $R^6$, fluorine, chlorine, bromine, cyano, $NR^6R^{6'}$, $OR^6$, $SR^6$ or hydroxy-$(C_1-C_6)$-alkyl-NH;

G is a radical of the formula II

W is a radical of the formula III

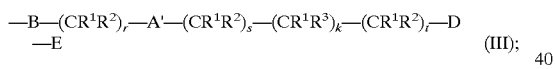

$G^a$ is a radical of the formula IIa

$W^a$ is a radical of the formula IIIa

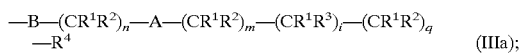

A, A' independently of one another are a direct bond, —C(O)NR$^5$—, —NR$^5$C(O)—, —C(O)—, —NR$^5$—, —O—, —S—, —SO—, —SO$_2$—, $(C_5-C_{14})$-arylene, where in the aryl radical one to five carbon atoms can be replaced by one to five heteroatoms, $(C_2-C_4)$-alkynylene, $(C_2-C_4)$-alkenylene, or a divalent radical of a 3- to 7-membered saturated or unsaturated ring which can contain one or two heteroatoms, such as, for example, nitrogen, sulfur or oxygen, and which can be monosubstituted or disubstituted by radicals from the group consisting of =O, =S and $R^3$;

$R^1$, $R^2$ independently of one another are hydrogen, flurine, chlorine, cyano, nitro, $(C_1-C_{10})$-alkyl, $(C_3-C_{14})$-cycloalkyl, $(C_3-C_{14})$-cycloalkyl-$(C_1-C_8)$-alkyl, $(C_5-C_{14})$-aryl, $(C_5-C_{14})$-aryl-$(C_1-C_8)$-alkyl, $R^6$—O—$R^7$, $R^6$—S(O)$_p$—$R^7$ or $R^6R^{6'}$N—$R^7$;

$R^3$ independently of one another is hydrogen, fluorine, chlorine, cyano, nitro, $(C_1-C_{18})$-alkyl, $(C_3-C_{14})$-cycloalkyl, $(C_3-C_{14})$-cycloalkyl-$(C_1-C_8)$-alkyl, $(C_5-C_{14})$-aryl, $(C_5-C_{14})$-aryl-$(C_1-C_8)$-alkyl, $R^6$—O—$R^7$, $R^6R^{6'}$N—$R^7$, $R^6C(O)$—O—$R^7$, $R^6C(O)R^7$, $R^6OC(O)R^7$, $R^6N(R^{6'})C(O)OR^7$, $R^6S(O)_pN(R^5)R^7$, $R^6OC(O)N(R^5)R^7$, $R^6C(O)N(R^5)R^7$, $R^6N(R^{6'})C(O)N(R^5)R^7$, $R^6N(R^{6'})S(O)_pN(R^5)R^7$, $R^6S(O)_pR^7$, $R^6SC(O)N(R^5)R^7$, $R^6N(R^{6'})C(O)R^7$ or $R^6N(R^{6'})S(O)_pR^7$, where alkyl can be monounsaturated or polyunsaturated and where furthermore alkyl and aryl can be monosubstituted or polysubstituted by fluorine, chlorine, bromine, cyano, $R^6R^{6'}NR^7$, nitro, $R^6OC(O)R^7$, $R^6C(O)R^7$, $R^6N(R^{6'})C(O)R^7$, $R^6N(R^{6'})S(O)_pR^7$, $R^6$ or $R^6$—O—$R^7$;

$R^4$ is $C(O)R^8$, $C(S)R^8$, $S(O)_pR^8$, $P(O)R^8R^{8'}$ or a radical of a four- to eight-membered saturated or unsaturated heterocycle which contains 1, 2, 3 or 4 heteroatoms from the group consisting of N, O, S, such as, for example, tetrazolyl, imidazolyl, pyrazolyl, oxazolyl, thiadiazolyl;

$R^5$ independently of one another is hydrogen, $(C_1-C_{10})$-alkyl, $(C_3-C_{14})$-cycloalkyl, $(C_3-C_{14})$-cycloalkyl-$(C_1-C_8)$-alkyl, $(C_5-C_{14})$-aryl or $(C_5-C_{14})$-aryl-$(C_1-C_8)$-alkyl;

$R^6$, $R^{6'}$ independently of one another are hydrogen, $(C_1-C_{18})$-alkyl, $(C_3-C_{14})$-cycloalkyl, $(C_3-C_{14})$-cycloalkyl-$(C_1-C_8)$-alkyl, $(C_5-C_{14})$-aryl, in which 1 to 5 carbon atoms can be replaced by heteroatoms such as N, O, S, or $(C_5-C_{14})$-aryl-$(C_1-C_8)$-alkyl, in which, in the aryl moiety, 1 to 5 carbon atoms can be replaced by heteroatoms such as N, O, S, or $R^6$ and $R^{6'}$, together with the atoms connecting them, form a ring system, in particular a 4- to 8-membered ring system which can optionally also contain additional, in particular one, two or three additional, heteroatoms from the group consisting of N, O, S and which can be saturated or unsaturated, in particular saturated, such as, for example, morpholine, thiomorpholine, piperazine, piperidine, pyrrolidine;

$R^7$ independently of one another is $(C_1-C_4)$-alkylene or a direct bond;

$R^8$, $R^{8'}$ independently of one another are hydroxyl, $(C_1-C_8)$-alkoxy, $(C_5-C_{14})$-aryl-$(C_1-C_8)$-alkoxy, $(C_5-C_{14})$-aryloxy, $(C_1-C_8)$-alkylcarbonyloxy-$(C_1-C_4)$-alkoxy, $(C_5-C_{14})$-aryl-$(C_1-C_8)$-alkylcarbonyloxy-$(C_1-C_8)$-alkoxy, $NR^6R^{6'}$, $(di((C_1-C_8)$-alkyl)amino)carbonylmethyloxy, $(di((C_5-C_{14})$-aryl-$(C_1-C_8)$-alkyl)-amino)carbonylmethyloxy, $(C_5-C_{14})$-arylamino, the radical of an amino acid, N—$((C_1-C_4)$-alkyl) piperidin-4-yloxy, 2-methylsulfonylethoxy, 1,3-thiazol-2-ylmethyloxy, 3-pyridylmethyloxy, 2-(di$((C_1-C_4)$-alkyl)amino)ethoxy or the radical $Q^-$ $(CH_3)_3N^+$—$CH_2$—$CH_2$—O—, in which $Q^-$ is a physiologically tolerable anion;

B is —O—, —S—, —NR$^5$—, —NR$^5$—C(O)—, —C(O)—NR$^5$—, a direct bond or a divalent radical of a 3- to 7-membered saturated or unsaturated ring which can contain one or two heteroatoms, such as, for example, nitrogen, sulfur or oxygen, and which can be monosubstituted or disubstituted by radicals from the group consisting of =O, =S and $R^3$;

D is a direct bond, —NR$^6$—, —C(O)—NR$^6$—, —NR$^6$—C(O)—, —S(O)$_u$——NR$^6$—, —NR$^6$—C(O)—NR$^6$—, —NR$^6$—C(S)—NR$^6$—, —NR$^6$—S(O)$_u$—NR$^6$—, —NR$^6$—C(O)O—, —NR$^6$—N=CR$^6$—, —NR$^6$—S(O)$_u$—, —(C$_5$-C$_{14}$)-aryl-CO—, —(C$_5$-C$_{14}$)-aryl-S(O)$_u$—, —N=CR$^6$—, —R$^6$C=N— or —R$^8$C=N—NR$^6$—, where the divalent radicals representing D are bonded to the group E via the free bond on the right side;

E is hydrogen, $R^6$—C(=$NR^6$)—$NR^{6'}$—, $R^6R^{6'}$N—C(=$NR^{6'}$)—, $R^6R^{6'}$N—C(=$NR^{6'}$)—$NR^6$— or a radical of a 4- to 11-membered, monocyclic or polycyclic, aromatic or nonaromatic ring system which can optionally contain 1, 2, 3 or 4 heteroatoms from the group consisting of N, O and S and can optionally be monosubstituted, disubstituted or trisubstituted by radicals from the group consisting of $R^3$, $R^5$, =O, =S and $R^6R^6$N—C(=$NR^6$)—, such as, for example, the following radicals:

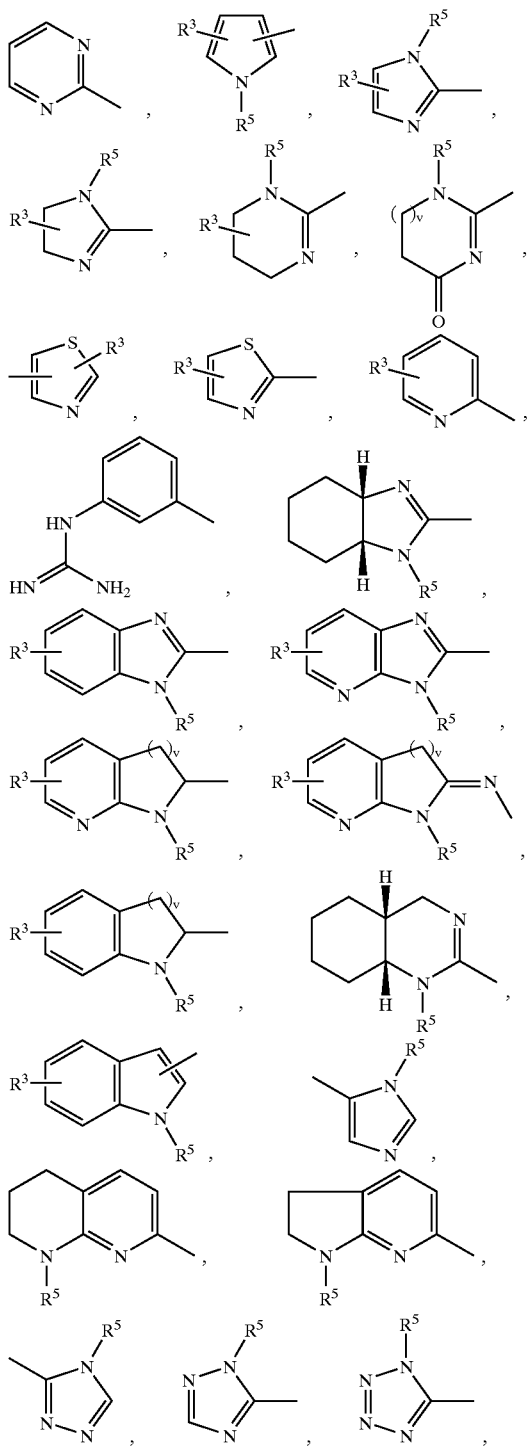

n is zero, one, two, three, four or five;
m is zero, one, two, three, four or five;
i is zero or one;
p independently of one another is zero, one or two;
q is zero, one or two;
r is zero, one, two, three, four, five or six;
s is zero, one, two, three, four or five;
t is zero, one, two, three, four or five;
k is zero or one;
u is one or two;
v is zero, one, two or three;
in all their stereoisomeric forms and mixtures thereof in all ratios, and their physiologically tolerable salts and their prodrugs;
where, instead of the purine structure shown in the formulae I and Ia, a 3-deazapurine structure, a 7-deazapurine structure or a 7-deaza-8-azapurine structure can also be present.

All radicals and indices which can occur several times in the compounds of the formulae I and Ia, for example the radicals $R^1$, $R^2$ and $R^3$ occurring in the radicals G and W and the radicals $R^5$, $R^6$, $R^{6'}$, $R^7$ and indices occurring therein, but also all other radicals and indices to which this applies, can each independently of one another have the meanings indicated. They can be identical or different. Likewise, heteroatoms in heterocycles or substituents in radicals which can be present several times independently of one another can have the meanings indicated and can be identical or different.

The alkyl radicals occurring in the substituents can be straight-chain or branched, saturated or mono- or polyunsaturated. This also applies if they carry substituents or occur as substituents of other radicals, for example in alkoxy radicals, alkoxycarbonyl radicals or aralkyl radicals. The same applies to the divalent alkylene radicals.

Examples of suitable ($C_1$–$C_{18}$)-alkyl radicals are: methyl, ethyl, propyl, butyl, pentyl, hexyl, heptyl, octyl, decyl, undecyl, dodecyl, tridecyl, hexadecyl, octadecyl, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Preferred alkyl radicals are methyl, ethyl, n-prbpyl, isopropyl, n-butyl, isobutyl, sec-butyl and tert-butyl.

Unsaturated alkyl radicals are, for example, alkenyl radicals such as vinyl, 1-propenyl, allyl, butenyl, 3-methyl-2-butenyl or alkynyl radicals such as ethynyl, 1-propynyl or propargyl. Alkenylene and alkynylene radicals can be straight-chain or branched. Examples of alkenylene radicals are vinylene or propenylene, examples of alkynylene radicals are ethynylene or propynylene.

Cycloalkyl radicals can be monocyclic, bicyclic or tricyclic. Monocyclic cycloalkyl radicals are, in particular, cyclopropyl, cyclobutyl, cyclopentyl, cyclohexyl, cycloheptyl and cyclooctyl, furthermore, for example, cyclononyl, cyclodecyl, cycloundecyl, cyclododecyl or cyclotetradecyl, which, however, can also all be substituted by, for example, $(C_1–C_4)$-alkyl. Examples of substituted cycloalkyl radicals which may be mentioned are 4-methylcyclohexyl and 2,3-dimethylcyclopentyl.

Bicyclic and tricyclic cycloalkyl radicals can be unsubstituted or can be substituted in any desired suitable positions by one or more oxo groups and/or one or more identical or different $(C_1–C_4)$-alkyl groups, for example methyl groups or isopropyl groups, preferably methyl groups. The free bond of the bicyclic or tricyclic radical can be located in any desired position of the molecule; the radical can thus be bonded via a bridgehead atom or via an atom in a bridge. The free bond can also be located in any desired stereochemical position, for example in an exo-position or an endo-position.

Examples of parent structures of bicyclic ring systems are norbornane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane).

Examples of parent structures of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

$(C_5–C_{14})$-aryl includes heterocyclic $(C_5–C_{14})$-aryl radicals in which ring carbon atoms are replaced by heteroatoms such as nitrogen, oxygen or sulfur, and carbocyclic $(C_6–C_{14})$-aryl radicals. Examples of carbocyclic aryl radicals are phenyl, naphthyl, biphenylyl, anthryl or fluorenyl, where 1-naphthyl, 2-naphthyl and in particular phenyl are preferred. Aryl radicals, in particular phenyl radicals, can be monosubstituted or polysubstituted, preferably monosubstituted, disubstituted or trisubstituted, by identical or different radicals from the group consisting of $(C_1–C_8)$-alkyl, in particular $(C_1–C_4)$-alkyl, $(C_1–C_8)$-alkoxy, in particular $(C_1–C_4)$-alkoxy, halogen, such as fluorine, chlorine and bromine, nitro, amino, trifluoromethyl, hydroxyl, methylenedioxy, cyano, hydroxycarbonyl, aminocarbonyl, $(C_1–C_4)$-alkoxycarbonyl, phenyl, phenoxy, benzyl, benzyloxy, $(R^9O)_2P(O)$—, $(R^9O)_2P(O)$—O— or tetrazolyl, where $R^9$ is hydrogen, $(C_1–C_{10})$-alkyl, $(C_6–C_{14})$-aryl or $(C_6–C_{14})$-aryl-$(C_1–C_8)$-alkyl. The same applies to the corresponding arylene radicals.

In monosubstituted phenyl radicals, the substituent can be located in the 2-position, the 3-position or the 4-position, the 3- and the 4-position being preferred. If phenyl is disubstituted, the substituents can be in the 1,2-, 1,3- or 1,4-position relative to one another. With respect to the linkage site, the substituents can be located in the 2,3-position, 2,4-position, 2,5-position, 2,6-position, 3,4-position or 3,5-position. Preferably, in disubstituted phenyl radicals the two substituents are arranged in the 3-position and the 4-position, relative to the linkage site.

Aryl groups or arylene groups can also be monocyclic or polycyclic aromatic ring systems in which 1, 2, 3, 4 or 5 ring carbon atoms are replaced by heteroatoms, such as, for example, 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzo-fused, cyclopenta-, cyclohexa- or cyclohepta-fused derivative of these radicals. These heterocycles can be substituted by the same substituents as the abovementioned carbocyclic aryl systems.

In the series of these aryl groups or of the corresponding arylene groups, monocyclic or bicyclic aromatic ring systems having 1, 2 or 3 heteroatoms from the group consisting of N, O, S, which can be unsubstituted or substituted by 1, 2 or 3 substituents from the group consisting of $(C_1–C_6)$-alkyl, $(C_1–C_6)$-alkoxy, fluorine, chlorine, nitro, amino, trifluoromethyl, hydroxyl, $(C_1–C_4)$-alkoxycarbonyl, phenyl, phenoxy, benzyloxy and benzyl, are preferred.

Particularly preferred here are monocyclic or bicyclic aromatic 5- to 10-membered ring systems having 1 to 3 heteroatoms from the group consisting of N, O, S, which can be substituted by 1 to 2 substituents from the group consisting of $(C_1–C_4)$-alkyl, $(C_1–C_4)$-alkoxy, phenyl, phenoxy, benzyl and benzyloxy.

Examples of saturated and unsaturated rings, in particular of 3- to 7-membered saturated or unsaturated rings which can contain one or two heteroatoms such as, for example, nitrogen, sulfur or oxygen and can optionally be monosubstituted or disubstituted by =O, =S or $R^3$, are cyclopropane, cyclobutane, cyclopentane, cyclohexane, cycloheptane, cyclopentene, cyclohexene, cycloheptene, tetrahydropyran, 1,4-dioxacyclohexane, morpholine, thiomorpholine, piperazine, piperidine, pyrrolidine, dihydroisoxazole, tetrahydroisoxazole, 1,3-dioxolane, 1,2-dithiolane, 2,3-dihydrofuran, 2,5dihydrofuran, tetrahydrofuran, 2,3-dihydrothiophene, 2,5-ihydrothiophene, 2-imidazoline, 3-imidazoline, 4-imidazoline, 2-oxazoline, 3-oxazoline, 4-oxazoline, 2-thiazoline, 3-thiazoline, 4-thiazoline, thiazolidine, α-thiapyran, α-pyran, γ-pyran.

The radical of an amino acid representing $R^8$ and/or $R^{8'}$ is, as usual in peptide chemistry, formally obtained by removing a hydrogen atom from the amino group of the amino acid. By means of the free bond on the amino group formally obtained hereby, the radical of the amino acid is then bonded, for example, to the CO group in the group CO—$R^8$. Amino acids can be natural or unnatural amino acids. α-Amino acids are preferred. Amino acids can exist in different stereochemical forms, for example as D- or L-amino acids, and in stereochemically homogeneous form or in the form of mixtures of stereoisomers. Amino acids which may be mentioned, for example, are (cf. Houben-Weyl, Methoden der organischen Chemie [Methods of Organic Chemistry], Volume XV/1 and 2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hpro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2- diphenylaminoacetic acid, 2-(p-tolyl)-2-phenylaminoacetic acid, 2-(p-chlorophenyl)aminoacetic acid;

Furthermore:

pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, hydroxypyrrolidine-2-carboxylic acid; all of which can be optionally substituted (see following formulae):

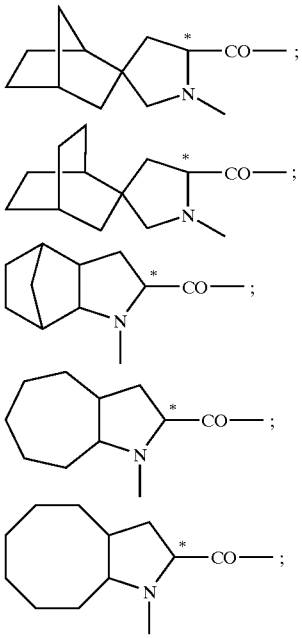

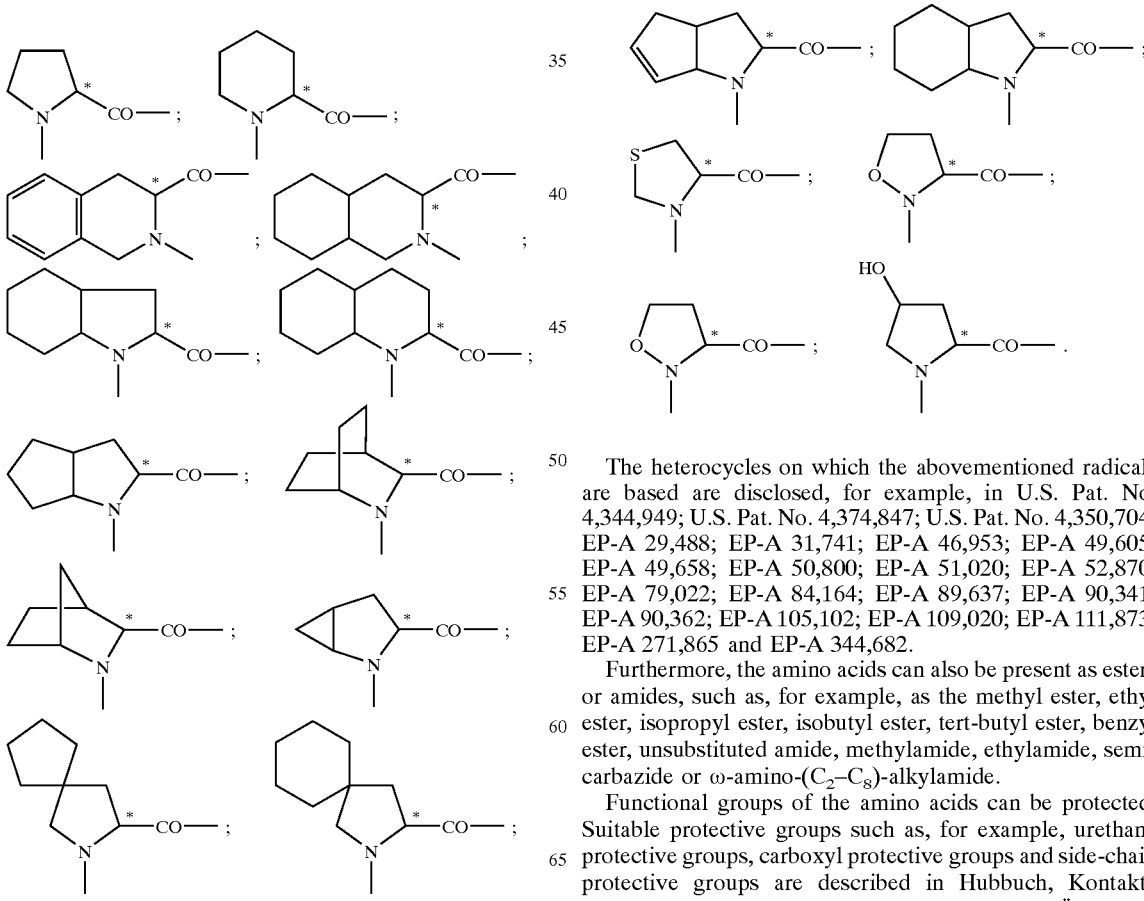

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Furthermore, the amino acids can also be present as esters or amides, such as, for example, as the methyl ester, ethyl ester, isopropyl ester, isobutyl ester, tert-butyl ester, benzyl ester, unsubstituted amide, methylamide, ethylamide, semicarbazide or ω-amino-($C_2$–$C_8$)-alkylamide.

Functional groups of the amino acids can be protected. Suitable protective groups such as, for example, urethane protective groups, carboxyl protective groups and side-chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z(NO₂), Z(Hal_n), Bobz, Iboc, Adpoc, Mboc, Acm, tert-Butyl, OBzl, ONbzl, OMbzl, Bzl, Mob, Pic, Trt.

The compounds of the formulae I and Ia according to the invention may be present as E/Z isomers. The invention relates to pure E isomers and pure Z isomers as well as to E/Z isomer mixtures in all ratios. The compounds of the formulae I and Ia can contain optically active carbon atoms which independently of one another may have the R- or S-configuration. They can be present in the form of pure enantiomers or pure diastereomers or in the form of enantiomer mixtures, for example in the form of racemates, or diastereomer mixtures. The invention relates to both pure enantiomers and enantiomer mixtures in all ratios and diastereomers and diastereomer mixtures in all ratios. Diastereomers, including E/Z isomers, can be separated into the individual isomers, for example, by chromatography. Racemates can be separated into the two enantiomers, for example, by chromatography on chiral phases or by resolution. If mobile hydrogen atoms are present, the present invention also includes all tautomeric forms of the compounds of the formulae I and Ia.

Physiologically tolerable salts of the compounds of the formulae I and Ia are, in particular, pharmaceutically utilizable or nontoxic, physiologically utilizable salts.

Such salts of compounds of the formulae I and Ia which contain acidic groups, for example carboxyl, are, for example, alkali metal salts or alkaline earth metal salts, such as, for example, sodium salts, potassium salts, magnesium salts and calcium salts, and also salts with physiologically tolerable quaternary ammonium ions and acid addition salts with ammonia and physiologically tolerable organic amines, such as, for example, triethylamine, ethanolamine or tris(2-hydroxyethyl)amine.

Compounds of the formulae I and Ia, which contain basic groups, for example one or more amino groups, amidino groups or guanidino groups, form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid.

A physiologically tolerable anion Q⁻, which is contained in the compounds of the formulae I and Ia when $R^8$ and/or $R^{8'}$ is the 2-trimethylammonio-ethoxy radical, is, in particular, a monovalent anion or an equivalent of a polyvalent anion of a nontoxic, physiologically utilizable, in particular also pharmaceutically utilizable, inorganic or organic acid, for example the anion or an anion equivalent of one of the abovementioned acids suitable for the formation of acid addition salts. Q⁻ can thus be, for example, one of the anions (or an anion equivalent) from the group consisting of chloride, sulfate, phosphate, acetate, citrate, benzoate, maleate, fumarate, tartrate, methanesulfonate and p-toluenesulfonate.

Salts can be obtained from the compounds of the formulae I and Ia by customary methods known to those skilled in the art, for example by combining the compounds of the formulae I and Ia with an inorganic or organic acid or base in a solvent or dispersant, or also from other salts by cation exchange or anion exchange. The present invention also includes all salts of the compounds of the formulae I and Ia which, because of low physiological tolerability, are not directly suitable for use in pharmaceuticals, but are suitable, for example, as intermediates for carrying out other chemical modifications of the compounds of the formulae I and Ia or as starting materials for the preparation of physiologically tolerable salts.

The present invention moreover includes all solvates of compounds of the formulae I and Ia, for example hydrates or adducts with alcohols, and also derivatives of the compounds of the formulae I and Ia, for example esters, prodrugs and metabolites, which act like the compounds of the formulae I and Ia. The invention relates in particular to prodrugs of the compounds of the formulae I and Ia, which can be converted into compounds of the formulae I and Ia under physiological conditions. Suitable prodrugs for the compounds of the formulae I and Ia, i.e. chemically modified derivatives of the compounds of the formulae I and Ia having properties which are improved in a desired manner, are known to those skilled in the art. More detailed information relating to prodrugs is found, for example, in Fleisher et al., Advanced Drug Delivery Reviews 19 (1996) 115–130; Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350. Suitable prodrugs for the compounds of the formulae I and Ia are especially ester prodrugs of acid groups, for example of carboxylic acid groups, in particular of a COOH group representing $R^4$, and also acyl prodrugs and carbamate prodrugs of acylatable nitrogen-containing groups such as amino groups, amidino groups or guanidino groups, in particular of the groups $R^6$—C(=NR⁶)—NR⁶—, $R^6R^{6'}N$—C(=NR⁶)—, $R^6R^{6'}N$—C(=NR⁶)—NR⁶—and the 4- to 11-membered, monocyclic or polycyclic, aromatic or non-aromatic ring system representing the group E. In the acyl prodrugs or carbamate prodrugs, a hydrogen atom located on a nitrogen atom is replaced one or more times, for example twice, in these groups by an acyl group or carbamate group. Suitable acyl groups and carbamate groups for the acyl prodrugs and carbamate prodrugs are, for example, the groups $R^6$—CO and $R^6O$—CO, in which $R^6$ has the meanings indicated above, i.e. hydrogen, $(C_1–C_{18})$-alkyl, $(C_3–C_{14})$-cycloalkyl, $(C_3–C_{14})$-cycloalkyl-$(C_1–C_8)$-alkyl, $(C_5–C_{14})$-aryl, in which 1 to 5 carbon atoms can be replaced by heteroatoms such as N, O, S, or $(C_5–C_{14})$-aryl-$(C_1–C_8)$-alkyl, in which 1 to 5 carbon atoms in the aryl moiety can be replaced by heteroatoms such as N, O, S, combinations of substituent meanings which in the individual case lead to unstable compounds, for example to unstable free carbamic acids, not being suitable. These prodrugs can be prepared by customary methods familiar to those skilled in the art for the preparation of acylamines and carbamates.

The present invention is furthermore not restricted to the compounds according to the formulae I and Ia having a purine parent structure, but also includes those compounds which instead of the purine parent structure shown in the formulae I and Ia have a 3-deazapurine structure, 7-deazapurine structure or 7-deaza-8-azapurine structure, i.e. compounds of the formulae Ib and Ic, Id and Ie and If and Ig.

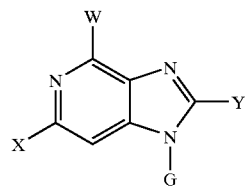

(Ib)

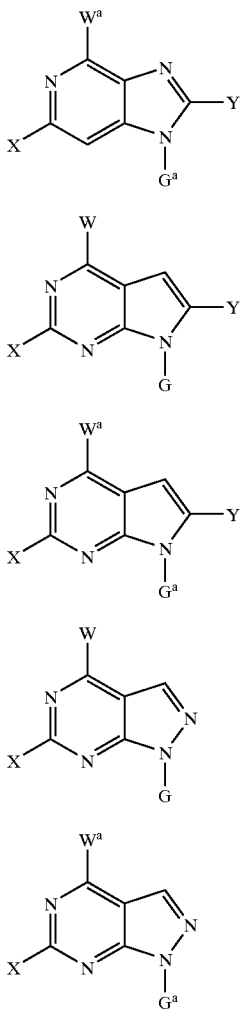

All the above and following details relating to the compounds of the formulae I and Ia apply to the compounds of the formulae Ib and Ic, Id and Ie, If and Ig correspondingly. If compounds of the formulae I and Ia are being discussed, then, if not stated otherwise, the deaza analogs and deaza-aza analogs of the formulae Ib and Ic, Id and Ie, If and Ig are also included. Preferably, in the compounds according to the invention the purine structure actually shown in formulae I and Ia is present, in which the nitrogen atoms are present in the 3-position and in the 7-position and a carbon atom with the group Y bonded thereto is present in the 8-position.

In the compounds of the formulae I and Ia, X is preferably hydrogen, $NR^6R^{6'}$, hydroxy-$(C_1-C_6)$-alkyl or NH—CO—$R^6$, particularly preferably hydrogen, $NR^6R^{6'}$ or NH—CO—$R^6$, very particularly preferably hydrogen or $NH_2$. Y is preferably hydrogen. $R^4$ is preferably $C(O)R^8$. Preferred compounds according to the invention are also those of the formulae I and Ia in which $R^3$ is $R^6R^{6'}N-R^7$, $R^6OC(O)N(R^5)R^7$, $R^6S(O)_pN(R^5)R^7$, $R^6C(O)N(R^5)R^7$ or $R^6N(R^{6'})C(O)N(R^5)R^7$, where p here is 1 or 2, in particular compounds in which $R^3$ is $R^6OC(O)N(R^5)R^7$ or $R^6S(O)_pN(R^5)R^7$ (where p=1 or 2); particularly preferred compounds here are those in which a lipophilic radical is contained in $R^3$, for example compounds in which $R^6$ and/or $R^{6'}$, for example in the group $R^6OC(O)N(R^5)R^7$, is $(C_4-C_{14})$-alkyl, $(C_5-C_{14})$-aryl-$(C_1-C_4)$-alkyl, for example benzyl, $(C_5-C_{14})$-cycloalkyl or $(C_5-C_{14})$-cycloalkyl-$(C_1-C_4)$-alkyl, preferred cycloalkyl radicals here in particular being the 1-adamantyl radical and the 2-adamantyl radical.

A preferred group of compounds according to the invention is formed by compounds of the formulae I and Ia in which:

X is hydrogen, $NH_2$, OH or NH—CO—$R^6$;

Y is hydrogen;

G is a radical of the formula II

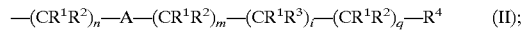

W is a radical of the formula III

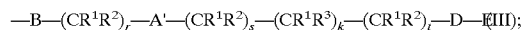

$G^a$ is a radical of the formula IIa

$W^a$ is a radical of the formula IIIa

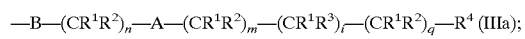

A, A' independently of one another are a direct bond, —C(O)$NR^5$—, —$NR^5$C(O)—, —C(O)—, —$NR^5$—, —O—, —S—, —SO—, —$SO_2$—, $(C_5-C_{14})$-arylene, it being possible in the aryl radical for one to five carbon atoms to be replaced by one to five heteroatoms, $(C_2-C_4)$-alkynylene, $(C_2-C_4)$-alkenylene, or a divalent radical of a 3- to 7-membered saturated or unsaturated ring, which can contain one or two heteroatoms, such as, for example, nitrogen, sulfur or oxygen and which can be monosubstituted or disubstituted by =O, =S or $R^3$;

$R^1$, $R^2$ independently of one another are H, fluorine, chlorine, CN, nitro, $(C_1-C_{10})$-alkyl, $(C_3-C_{14})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $R^6$—O—$R^7$, $R^6$—$S(O)_p$—$R^7$ or $R^6R^{6'}N$—$R^7$;

$R^3$ independently of one another is H, fluorine, chlorine, CN, nitro, $(C_1-C_{14})$-alkyl, $(C_3-C_{14})$-cycloakyl, $(C_3-C_{14})$-cycloalkyl-$(C_1-C_8)$-alkyl, $(C_5-C_{14})$-aryl, $(C_5-C_{14})$-aryl-$(C_1-C_8)$-alkyl, $R^6$—O—$R^7$, $R^6$—$S(O)_n$—$R^7$, $R^6R^{6'}N$—$R^7$, $R^6CO_2R^7$, $R^6COR^7$, $R^6OC(O)R^7$, $R^6N(R^5)C(O)OR^7$, $R^6S(O)_pN(R^5)R^7$, $R^6OC(O)N(R^5)R^7$, $R^6C(O)N(R^5)R^7$, $R^6N(R^5)C(O)N(R^5)R^7$, $R^6N(R^5)S(O)_pN(R^5)R^7$, $R^6S(O)_pR^7$, $R^6SC(O)N(R^5)R^7$, $R^6C(O)R^6$, $R^6N(R^5)C(O)R^7$ or $R^6N(R^5)S(O)_p$ $R^7$, it being possible for alkyl to be monounsaturated or polyunsaturated and it furthermore being possible for alkyl and aryl to be monosubstituted or polysubstituted by fluorine, chlorine, bromine, CN, $R^6N(R^5)R^7$, $R^6R^{6'}NR^7$, nitro, $R^6OC(O)R^7$, $R^6C(O)R^7$, $R^6N(R^5)C(O)R^7$, $R^6N(R^5)S(O)_pR^7$, $R^6$, $R^6$—O—$R^7$;

$R^4$ is $C(O)R^8$, $C(S)R^8$, $S(O)_pR^8$, $POR^8R^{8'}$, an L- or D-amino acid or a four- to eight-membered, saturated or unsaturated heterocycle which contains 1, 2, 3 or 4 heteroatoms from the group consisting of N, O, S, such as, for example, tetrazolyl, imidazolyl, pyrazolyl, oxazolyl, thiadiazolyl;

$R^5$ is H, $(C_1-C_{10})$-alkyl, $(C_3-C_{14})$-cycloalkyl, $(C_3-C_{14})$-cycloalkyl-$(C_1-C_8)$-alkyl, $(C_5-C_{14})$-aryl or $(C_5-C_{14})$-aryl-$(C_1-C_8)$-alkyl;

$R^6$, $R^{6'}$ independently of one another are H, $(C_1-C_8)$-alkyl, $(C_3-C_{14})$-cycloalkyl, $(C_3-C_{14})$-cycloalkyl- ($C_1$–$C_8$)-alkyl, ($C_5$–$C_{14}$)-aryl, it being possible for 1–5 carbon atoms to be replaced by heteroatoms, or ($C_5$–$C_4$)-aryl-($C_1$–$C_8$)-alkyl, it being possible for 1–5 carbon atoms in the aryl moiety to be replaced by heteroatoms, or $R^6$ and $R^{6'}$, together with the atoms connecting them, form a ring system which can optionally also contain further heteroatoms from the group consisting of N, S, O, such as, for example, morpholine, piperazine, piperidine, pyrrolidine;

$R^7$ independently of one another is ($C_1$–$C_4$)-alkylene or a direct bond;

$R^8$, $R^{8'}$ independently of one another are OH, ($C_1$–$C_8$)-alkoxy, ($C_5$–$C_{14}$)-aryl-($C_1$–$C_8$)-alkoxy, ($C_5$–$C_{14}$)-aryloxy, ($C_1$–$C_8$)-alkylcarbonyloxy-($C_1$–$C_4$)-alkoxy, ($C_5$–$C_{14}$)-aryl-($C_1$–$C_8$)-alkylcarbonyloxy($C_1$–$C_6$)-alkoxy, $NR^6R^6$, ($C_1$–$C_8$)-dialkylaminocarbonylmethyloxy, ($C_5$–$C_{14}$)-aryl-($C_1$–$C_8$)-dialkylaminocarbonylmethyloxy, ($C_5$–$C_{14}$)-arylamino or an L- or D-amino acid;

B is O, S, $NR^5$, —$NR^5$-C(O)—, —C(O)—$NR^5$—, a direct bond or a divalent radical of a 3- to 7-membered saturated or unsaturated ring which can contain one or two heteroatoms, such as, for example, nitrogen, sulfur or oxygen, and which can be monosubstituted or disubstituted by =O, =S or $R^3$;

D is a direct bond, —$NR^6$—, —C(O)—$NR^6$—, —$NR^6$—C(O)—, —$SO_2NR^6$—, —$NR^6$—C(O)—$NR^6$—, —$NR^6$—C(S)—$NR^6$—, —$NR^6$—S(O)$_u$—$NR^6$—, —$NR^6$—C(O)O—, —$NR^6$—N=C$R^6$—$NR^6$—S(O)$_u$—, —($C_5$–$C_{14}$)-aryl—CO—, —($C_5$–$C_{14}$)-aryl-S(O)$_u$—, —N=C$R^6$, —$R^6$C=N— or —$R^6$C=N—$NR^6$—;

E is hydrogen, $R^6$—C(=$NR^6$)$NR^6$—, $R^6R^{6'}$N—C(=$NR^6$)—, $R^6R^{6'}$N—C(=$NR^6$)—$NR^6$—, or a 4- to 11-membered, mono- or polycyclic, aromatic or non-aromatic ring system which can optionally contain 1–4 heteroatoms from the group consisting of N, O and S and can optionally be monosubstituted to trisubstituted by $R^3$, $R^5$, =O, =S or $R^6R^{6'}$N—C(=$NR^6$)—, such as, for example, the radicals indicated with their structural formulae in the above definition of E;

n is zero, one, two, three, four or five;

m is zero, one, two, three, four or five;

i is zero or one;

p independently of one another is zero, one or two;

q independently of one another is zero, one or two;

r is zero, one, two, three, four, five or six;

s is zero, one, two, three, four or five;

t is zero, one, two, three, four or five;

k is zero or one;

u is one or two;

v in the radicals indicated in the above definition of E is the numbers zero, one, two or three;

in all their stereoisomeric forms and mixtures thereof in all ratios, and their physiologically tolerable salts, where, in this group of preferred compounds, the analogs having a 3-deazapurine structure, 7-deazapurine structure or 7-deaza-8-azapurine structure are not included.

A further group of preferred compounds is formed by compounds of the formulae I and Ia in which:

X is hydrogen, $NR^6R^{6'}$, hydroxy-($C_1$–$C_6$)-alkyl-NH or NH—CO—$R^6$;

Y is hydrogen;

G is a radical of the formula II $$-(CR^1R^2)_n-A-(CR^1R^2)_m-(CR^1R^3)_t-(CR^1R^2)_q-R^4 \quad (II);$$

W is a radical of the formula III $$-B-(CR^1R^2)_r-A'-(CR^1R^2)_s-(CR^1R^3)_k-(CR^1R^2)_t-D-E (III);$$

$G^a$ is a radical of the formula IIa $$-(CR^1R^2)_r-A'-(CR^1R^2)_s-(CR^1R^3)_k-(CR^1R^2)_t-D-E \quad (IIa);$$

$W^a$ is a radical of the formula IIIa $$-B-(CR^1R^2)_n-A-(CR^1R^2)_m-(CR^1R^3)_t-(CR^1R^2)_q-R^4 (IIIa);$$

A, A' independently of one another are a direct bond, —C(O)$NR^5$—, —$NR^5$C(O)—, —C(O)—, —$NR^5$—, —O—, —S—, —SO—, —$SO_2$—, ($C_5$–$C_{14}$)-arylene, it being possible for one to three carbon atoms in the aryl radical to be replaced by one to three heteroatoms from the group consisting of O, N, S, ($C_2$–$C_4$)-alkynylene or ($C_2$–$C_4$)-alkenylene;

$R^1$, $R^2$ independently of one another are hydrogen, fluorine, cyano, ($C_1$–$C_4$)-alkyl, ($C_5$–$C_6$)-aryl $C_5$–$C_6$)-aryl-($C_1$–$C_4$)-alkyl, $R^6$—O—$R^7$ or $R^6R^{6'}$N—$R^7$;

$R^3$ independently of one another is hydrogen, ($C_1$–$C_{18}$)-alkyl, ($C_3$–$C_{14}$)-cycloalkyl, ($C_3$–$C_{14}$)-cycloalkyl-($C_1$–$C_8$)-alkyl, ($C_5$–$C_{14}$)-aryl,($C_5$–$C_{14}$)-aryl-($C_1$–$C_8$)-alkyl, $R^6R^{6'}$N—$R^7$, $R^6$C(O)$R^7$, $R^6$S(O)$_p$N($R^5$)$R^7$, $R^6$OC(O)N($R^5$)$R^7$, $R^6$C(O)N($R^5$)$R^7$, $R^6$N($R^{6'}$)C(O)N($R^5$)$R^7$, $R^6$N($R^{6'}$)S(O)$_p$N($R^5$)$R^7$ or $R^6$N($R^{6'}$)C(O)$R^7$, it being possible for alkyl to be monounsaturated or polyunsaturated and it furthermore being possible for alkyl and aryl to be monosubstituted or polysubstituted by fluorine, chlorine, bromine, cyano, $R^6R^{6'}$N$R^7$, nitro, $R^6$OC(O)$R^7$, $R^6$C(O)$R^7$, $R^6$N($R^{6'}$)C(O)$R^7$, $R'$N($R^{6'}$)S(O)$_p$$R^{7,\ R6}$ or $R^6$O$R^7$;

$R^4$ is C(O)$R^8$;

$R^5$ independently of one another is hydrogen or ($C_1$–$C_4$)-alkyl;

$R^6$, $R^{6'}$independently of one another are hydrogen, ($C_1$–$C_{18}$)-alkyl, ($C_3$–$C_{14}$)-cycloalkyl, ($C_3$–$C_{14}$)-cycloalkyl-($C_1$–$C_8$)-alkyl, ($C_5$–$C_{14}$)-aryl, in which one to three carbon atoms can be replaced by one to three heteroatoms from the group consisting of N, S, O, or are ($C_5$–$C_{14}$)-aryl-($C_1$–$C_8$)-alkyl, in which one to three carbon atoms in the aryl moiety can be replaced by one to three heteroatoms from the group consisting of N, S, O, or $R^6$ and $R^{6'}$, together with the atoms connecting them, form a ring system which can optionally also contain additional heteroatoms from the group consisting of N, S, O, such as, for example, morpholine, piperazine, piperidine, pyrrolidine;

$R^7$ independently of one another is ($C_1$–$C_2$)-alkylene or a direct bond;

$R^8$ independently of one another is hydroxyl, ($C_1$–$C_4$)-alkoxy, ($C_5$–$C_{14}$)-aryl-($C_1$–$C_4$)-alkoxy, ($C_5$–$C_{14}$)-aryloxy, ($C_1$–$C_8$)-alkylcarbonyloxy-($C_1$–$C_4$)-alkoxy, ($C_5$–$C_{14}$)-aryl-($C_1$–$C_4$)-alkylcarbonyloxy-($C_1$–$C_4$)-alkoxy or the radical of an amino acid;

B is —O—, —S—, —$NR^5$—, a direct bond or a divalent radical of a 3- to 7-membered saturated or unsaturated ring which can contain one or two heteroatoms, such as, for example, nitrogen, sulfur or oxygen and which can be monosubstituted or disubstituted by radicals from the group consisting of =O, =S and $R^3$;

D is a direct bond, —$NR^6$—, —C(O)—$NR^6$—, —$NR^6$—C(O)—, —$NR^6$—C(O)—$NR^6$—, —$NR^6$—C(O)O—, —NR$^6$—N=CR$^6$—, —R$^6$C=N—NR$^6$—, —N=CR$^6$— or —R$^6$C=N—, where the divalent radicals representing D are bonded to the group E via the free bond on the right side;

E is hydrogen, R$^6$—C(=NR$^6$)—NR$^{6'}$—, R$^6$R$^{6'}$N—C(=NR$^6$)—, R$^6$R$^{6'}$N—C(=NR$^{6'}$)—NR$^6$— or a radical from the group consisting of

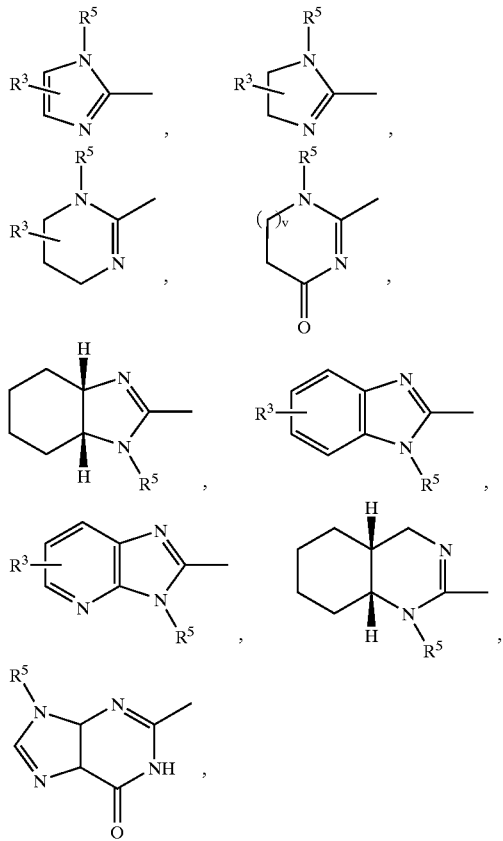

which can optionally be monosubstituted to trisubstituted by radicals from the group consisting of R$^3$, R$^5$, =O, =S and R$^6$R$^{6'}$N—C(=NR$^6$)—;

n is one, two, three or four;
m is zero or one;
is zero or one;
q is zero or one;
p independently of one another is zero, one or two;
r is zero, one, two, three, four or five;
s is zero, one or two;
t is zero, one or two;
k is zero or one;
v is zero, one, two or three;
in all their stereoisomeric forms and mixtures thereof in all ratios, and their physiologically tolerable salts and their prodrugs.

Particularly preferred compounds of the formulae I and Ia are those in which:

X is hydrogen, NR$^6$R$^{6'}$ or NH—CO—R$^6$;
Y is hydrogen;
G is a radical of the formula II —(CR$^1$R$^2$)$_n$—A—(CR$^1$R$^2$)$_m$—(CR$^1$R$^3$)$_t$—(CR$^1$R$^2$)$_q$—R$^4$  (II);

W is a radical of the formula III

—B—(CR$^1$R$^2$)$_r$—A'—(CR$^1$R$^2$)$_s$—(CR$^1$R$^3$)$_k$—(CR$^1$R$^2$)$_t$— D—E  (III);

G$^a$ is a radical of the formula IIa

—(CR$^1$R$^2$)$_r$—A'—(CR$^1$R$^2$)$_s$—(CR$^1$R$^3$)$_k$—(CR$^1$R$^2$)$_t$—D—E  (IIa);

W$^a$ is a radical of the formula IIIa

—B—(CR$^1$R$^2$)$_n$—A—(CR$^1$R$^2$)$_m$—(CR$^1$R$^3$)$_t$—(CR$^1$R$^2$)$_q$—R$^4$  (IIIa);

A, A' independently of one another are a direct bond, —C(O)NR$^5$—, —NR$^5$C(O)— or (C$_5$–C$_6$)-arylene, it being possible for one to two carbon atoms in the aryl radical to be replaced by nitrogen atoms;

R$^1$, R$^2$ are hydrogen;

R$^3$ independently of one another is hydrogen, (C$_1$–C$_{10}$)-alkyl, (C$_3$–C$_{14}$)-cycloalkyl, (C$_3$–C$_{14}$)-cycloalkyl-(C$_1$–C$_8$)-alkyl, (C$_5$–C$_{14}$)-aryl, (C$_5$–C$_4$)-aryl, (C$_5$–C$_{14}$)-aryl-(C$_1$–C$_8$)-alkyl, R$^6$R$^{6'}$N—R$^7$, R$^6$OC(O)N(R$^5$)R$^7$, R$^6$C(O)N(R$^5$)R$^7$, R$^6$N(R$^6$')C(O)N(R$^5$)R$^7$, R$^6$C(O)R$^7$ or R$^6$N(R$^{6'}$)C(O)R$^7$, it being possible for alkyl to be monounsaturated or polyunsaturated and it furthermore being possible for alkyl and aryl to be monosubstituted or polysubstituted by fluorine, chlorine, bromine, cyano, R$^6$R$^{6'}$NR$^7$, R$^6$C(O)R$^7$, R$^6$N(R$^{6'}$)C(O)R$^7$, R$^6$ or R$^6$OR$^7$;

R$^4$ is C(O)R$^8$;

R$^5$ independently of one another is hydrogen or (C$_1$–C$_4$)-alkyl;

R$^6$, R$^{6'}$ independently of one another are hydrogen, (C$_1$–C$_8$)-alkyl, (C$_3$–C$_{12}$)-cycloalkyl, (C$_3$–C$_{12}$)-cycloalkyl-(C$_1$–C$_8$)-alkyl, (C$_5$–C$_{14}$)-aryl, in which one to three carbon atoms can be replaced by one to three heteroatoms from the group consisting of N, S, O, or are (C$_5$–C$_{14}$)-aryl-(C$_1$–C$_8$)-alkyl, in which one to three carbon atoms in the aryl moiety can be replaced by one to three heteroatoms from the group consisting of N, S, O;

R$^7$ is a direct bond;

R$^8$ independently of one another is hydroxyl, (C$_1$–C$_4$)-alkoxy, (C$_5$–C$_{14}$)-aryl-(C$_1$–C$_4$)-alkoxy, (C$_5$–C$_{14}$)-aryloxy, (C$_1$–C$_8$)-alkylcarbonyloxy-(C$_1$–C$_4$)-alkoxy, (C$_5$–C$_{14}$)-aryl-(C$_1$–C$_4$)-alkylcarbonyloxy-(C$_1$–C$_4$)-alkoxy or the radical of an amino acid;

B is —O—, —S—, —NR$^5$—, a direct bond or a divalent radical of a 3- to 7-membered saturated or unsaturated ring, which can contain one or two heteroatoms, such as, for example, nitrogen, sulfur or oxygen and which can be monosubstituted or disubstituted by radicals from the group consisting of =O, =S and R$^3$;

D is a direct bond, —NR$^6$—, —C(O)—NR$^6$— or —NR$^6$—C(O)—;

E is hydrogen, R$^6$—C(=NR$^6$)—NR$^{6'}$—, R$^6$R$^{6'}$N—C(=NR$^6$)—, R$^6$R$^{6'}$N—C(=NR$^{6'}$)—NR$^6$— or a radical from the group consisting of

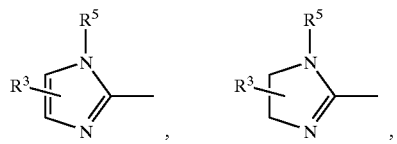

-continued

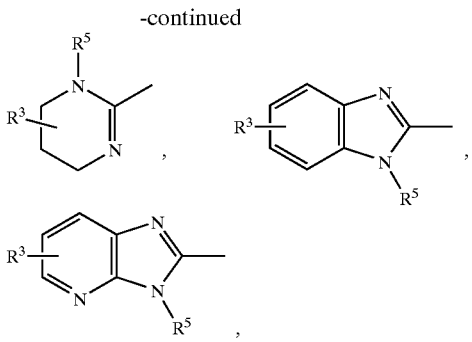

which can optionally be monosubstituted to trisubstituted by radicals from the group consisting of $R^3$, $R^5$, =O, =S and $R^6R^{6'}N-C(=NR^6)-$;

r is zero, one, two, three, four or five;

s is zero or one;

t is zero or one;

k is zero or one;

n is one, two, three or four;

m is zero or one;

i is zero or one;

q is zero or one;

in all their stereoisomeric forms and mixtures thereof in all ratios, and their physiologically tolerable salts and their prodrugs.

Particularly preferred compounds of the formula I are furthermore those in which:

X is hydrogen, $NR^6R^{6'}$ or $NH-CO-R^6$;

Y is hydrogen;

G is a radical of the formula II

W is a radical of the formula III

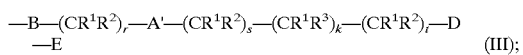

A, A' are a direct bond;

$R^1$, $R^2$ independently of one another are hydrogen, $(C_1-C_4)$-alkyl, $(C_5-C_6)$-aryl or $(C_5-C_6)$-aryl-$(C_1-C_4)$-alkyl;

$R^3$ independently of one another is hydrogen, $(C_1-C_{18})$-alkyl, $(C_3-C_{14})$-cycloalkyl, $(C_3-C_{14})$ cycloalkyl-$(C_1-C_8)$-alkyl, $(C_5-C_{14})$-aryl, $(C_5-C_{14})$-aryl-$(C_1-C_8)$-alkyl, $R^6R^{6'}N-R^7$, $R^6OC(O)N(R^5)R^7$, $R^6SO_2N(R^5)R^7$, $R^6C(O)N(R^5)R^7$, $R^6N(R^{6'})C(O)N(R^5)R^7$, $R^6C(O)R^7$ or $R^6N(R^{6'})C(O)R^7$, it being possible for alkyl to be monounsaturated or polyunsaturated and it furthermore being possible for alkyl and aryl to be monosubstituted or polysubstituted by fluorine, chlorine, bromine, cyano, $R^6R^{6'}NR^7$, $R^6C(O)R^7$, $R^6N(R^{6'})C(O)R^7$, $R^6$ or $R^6OR^7$;

$R^4$ is $C(O)R^8$;

$R^5$ independently of one another is hydrogen or $(C_1-C_4)$-alkyl;

$R^6$, $R^{6'}$ independently of one another are hydrogen, $(C_1-C_{18})$-alkyl, $(C_3-C_{12})$-cycloalkyl, $(C_3-C_{12})$-cycloalkyl-$(C_1-C_8)$-alkyl, $(C_5-C_{14})$-aryl, in which 1 to 3 carbon atoms can be replaced by 1 to 3 heteroatoms from the group consisting of N, S, O, or are $(C_5-C_{14})$-aryl-$(C_1-C_8)$-alkyl, in which 1 to 3 carbon atoms in the aryl radicals can be replaced by 1 to 3 heteroatoms from the group consisting of N, S, O, and it also being possible for $R^6$ and $R^{6'}$, together with the atoms connecting them, to form a ring system which can optionally also contain additional, in particular one, two or three, heteroatoms from the group consisting of N, S, O;

$R^7$ is a direct bond;

$R^8$ independently of one another is hydroxyl, $(C_1-C_4)$-alkoxy, $(C_5-C_{14})$-aryl-$(C_1-C_4)$-alkoxy, $(C_5-C_{14})$-aryloxy, $(C_1-C_8)$-alkylcarbonyloxy$(C_1-C_4)$-alkoxy or $(C_5-C_{14})$-aryl-$(C_1-C_4)$-alkylcarbonyloxy$(C_1-C_4)$-alkoxy;

B is 1,4-piperidinediyl or 1,4-piperazinediyl, where in the case of the 1,4-piperidinediyl radical the nitrogen atom of the piperidine is bonded to the purine structure;

D is a direct bond, $-NR^6-$, $-C(O)-NR^6-$ or $-NR^6-C(O)-$;

E is hydrogen, $R^6-C(=NR^6)NR^{6'}-$, $R^6R^{6'}N-C(=NR^6)-$, $R^6R^{6'}N-C-(=NR^{6'})-NR^6-$ or a radical from the group consisting of

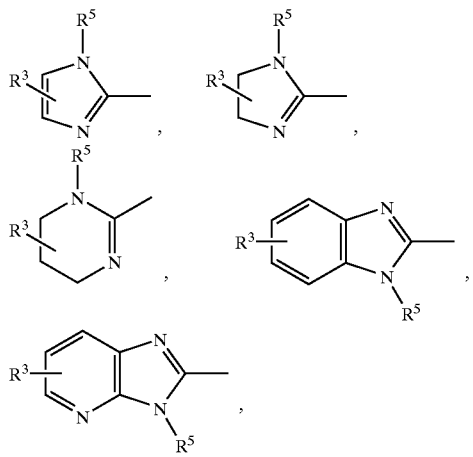

which can optionally be monosubstituted to trisubstituted by radicals from the group consisting of $R^3$, $R^5$, =O, =S and $R^6R^{6'}N-C(=NR^6)-$;

r is zero, one or two;

s is zero or one;

t is zero or one;

k is zero or one;

n is zero, one or two;

m is zero or one;

i is zero or one;

q is zero or one;

in all their stereoisomeric forms and mixtures thereof in all ratios, and their physiologically tolerable salts and their prodrugs.

Very particularly preferred compounds of the formula I are those in which:

X is hydrogen;

Y is hydrogen;

G is a radical of the formula II

W is a radical of the formula III

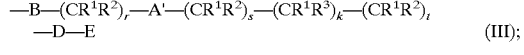

A, A' are a direct bond;

$R^1$, $R^2$ independently of one another are hydrogen or ($C_1$–$C_2$)-alkyl, in particular hydrogen;

$R^3$ is $R^6R^{6'}N$—$R^7$, $R^6OC(O)N(R^5)R^7$, $R^6SO_2N(R^5)R^7$, $R^6C(O)N(R^5)R^7$ or $R^6N(R^{6'})C(O)N(R^5)R^7$, in particular $R^6OC(O)N(R^5)R^7$;

$R^4$ is $C(O)R^8$;

$R^5$ is hydrogen or ($C_1$–$C_2$)-alkyl, in particular hydrogen;

$R^6$, $R^{6'}$ independently of one another are hydrogen, ($C_1$–$C_{18}$)-alkyl, ($C_3$–$C_{12}$)-cycloalkyl, ($C_3$–$C_{12}$) cycloalkyl-($C_1$–$C_8$)-alkyl, ($C_5$–$C_{14}$)-aryl, in which 1 to 3 carbon atoms can be replaced by 1 to 3 heteroatoms from the group consisting of N, S, O, or are ($C_5$–$C_{14}$)-aryl-($C_1$–$C_8$)-alkyl, in which 1 to 3 carbon atoms in aryl radicals can be replaced by 1 to 3 heteroatoms from the group consisting of N, S, O, and it also being possible for $R^6$ and $R^{6'}$, together with the atoms connecting them, to form a ring system which can optionally also contain additional, in particular one, two or three, heteroatoms from the group consisting of N, S, O;

$R^7$ is a direct bond;

$R^8$ is hydroxyl, ($C_1$–$C_4$)-alkoxy, ($C_5$–$C_{14}$)-aryl-($C_1$–$C_4$)-alkoxy, ($C_5$–$C_{14}$)-aryloxy, ($C_1$–$C_8$)-alkylcarbonyloxy ($C_1$–$C_4$)-alkoxy or ($C_5$–$C_{14}$)-aryl-($C_1$–$C_4$)-alkylcarbonyloxy-($C_1$–$C_4$)-alkoxy, in particular hydroxyl or ($C_1$–$C_4$)-alkoxy;

B is 1,4-piperidinediyl, where the nitrogen atom of the piperidine is bonded to the purine structure;

D is —$NR^6$— or —$C(O)$—$NR^6$—, where in the group —$C(O)$—$NR^6$— the nitrogen atom is bonded to the group E;

E is $R^6R^{6'}N$—$C(=NR^{6'})$— or a radical from the group consisting of

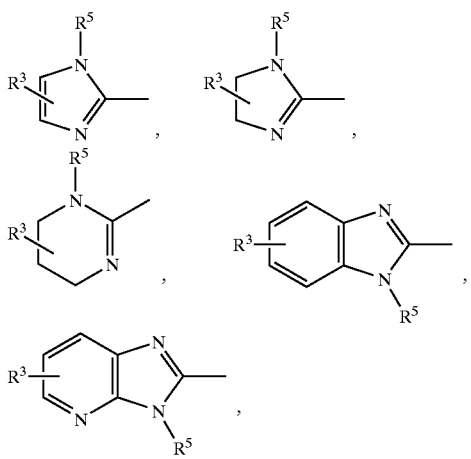

which can optionally be monosubstituted to trisubstituted by radicals from the group consisting of $R^3$, $R^5$, =O, =S and $R^6R^{6'}N$—$C(=NR^6)$—;

r is zero or one;
s is zero;
t is zero;
k is zero;
n is one;
m is zero;
i is one;
q is zero;

in all their stereoisomeric forms and mixtures thereof in all ratios, and their physiologically tolerable salts and their prodrugs.

Especially preferred compounds according to the invention are the compounds of the formula Ih

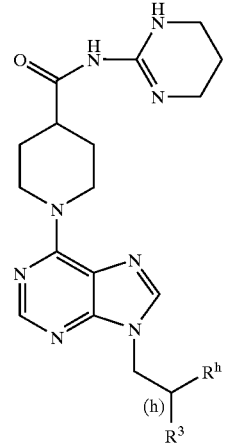

(Ih)

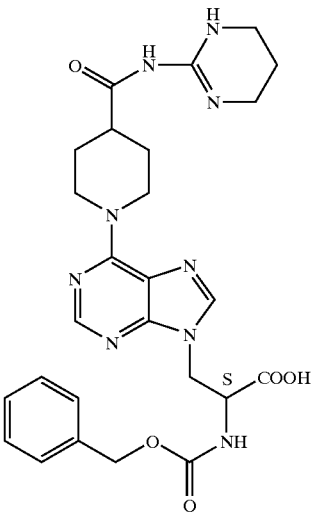

(Ik)

in which $R^3$ is $R^6R^{6'}N$—$R^7_1$, $R^6OC(O)N(R^5)R^7$, $R^6SO_2N(R^5)R^7$, $R^6C(O)N(R^5)R^7$ or $R^6N(R^{6'})C(O)N(R^5)R^7$, in particular $R^6OC(O)N(R^5)R^7$, and $R^h$ is the carboxylic acid group COOH or a carboxylic acid derivative, for example an ester such as, for example, a ($C_1$–$C_4$)-alkyl ester, i.e. for example the group COO—($C_1$–$C_4$)-alkyl; in all their stereowsomeric forms and mixtures thereof in all ratios, and their physiologically tolerable salts and their prodrugs. In compounds of the formula Ih in which $R^7$ is a direct bond, the stereochemical center (h) in the formula Ih preferably has the S-configuration. Compounds of the formula Ih in which $R^7$ is a direct bond can be named as 2-amino-3-(6-(4-(1,4,5,6-tetrahydropyrimidin-2-ylcarbamoyl)piperidin-1-yl) purin-9-yl)propionic acid and derivatives thereof, for example esters, optionally substituted on the 2-amino group. A particularly especially preferred compound is 2S-benzyloxycarbonylamino-3-(6-(4-(1,4,5,6-tetrahydropyrimidin-2-yl-carbamoyl)-piperidin-1-yl)-purin-9-yl)-propionic acid of the formula Ik and its physiologically tolerable salts and its prodrugs.

Compounds of the formulae I and Ia can generally be prepared, for example in the course of a convergent synthesis, by linkage of two or more fragments which can be derived retrosynthetically from the formulae I and Ia. In the preparation of the compounds of the formulae I and Ia, it can generally be advantageous or necessary in the course of the synthesis to introduce functional groups which could lead to undesired reactions or side reactions in the respective synthesis step, in the form of precursors which are later converted into the desired functional groups, or temporarily to block functional groups by a protective group strategy suited to the synthesis problem, what is known to those skilled in the art (Greene, Wuts, Protective Groups in Organic Synthesis, Wiley, 1991).

The present invention also relates to processes for the synthesis of the compounds of the formula I, which comprise carrying out one or more of the following steps for the synthesis of the compounds of the formula I.

a1) A compound of the formula IV, (IV)

in which

L1 is a customary leaving group known to those skilled in the art, for example chlorine, bromine, iodine, OTos or OMes, preferably chlorine or bromine, and X and Y are as defined above, but functional groups can optionally also be present in the form of precursors or can temporarily be protected by a protective group, is reacted with a compound of the formula V $$L2-(CR^1R^2)_n-A-(CR^1R^2)_m-(CR^1R^3)_i-(CR^1R^2)_q-R^{10} \quad (V)$$

in which $R^1$, $R^2$, $R^3$, A, n, m, i and q are as defined above, $R^{10}$ is defined as $R^4$ above, but is optionally protected by a protective group, for example for $R^4$=COOH by a tert-butyl or a methyl or ethyl protective group, L2 is hydroxyl or a leaving group known to those skilled in the art, for example chlorine, bromine, iodine, OTos, OMes or OTf, to give a compound of the formula VI (VI)

in which $R^{11}$ is $-(CR^1R^2)_n-A-(CR^1R^2)_m-(CR^1R^3)_i-(CR^1R^2)_q-R^{10}$ and for which otherwise the above meanings apply, the reaction being carried out according to methods known to those skilled in the art (see source literature in J. March, Advanced Organic Chemistry, Fourth Edition, Wiley, 1992). Preferably, the reaction is carried out in a suitable organic solvent or diluent, for example DCM, CHCl$_3$, THF, diethyl ether, n-heptane, n-hexane, n-pentane, cyclohexane, diisopropyl ether, methyl tert-butyl ether, acetonitrile, DMF, DMSO, dioxane, toluene, benzene, ethyl acetate or a mixture of these solvents, if appropriate with addition of a base such as, for example, butyllithium, lithium diisopropylamide (LDA), sodium hydride, sodium amide, potassium tert-butoxide, CaCO$_3$, Cs$_2$CO$_3$, triethylamine, diisopropylethylamine or complex bases (sodium amide/R$^{12}$ONa, where $R^{12}$ is (C$_2$–C$_6$)-alkyl or CH$_3$CH$_2$OCH$_2$CH$_2$). For L2=OH, the reaction can be carried out, for example, by the conditions described for the Mitsunobu reaction (Hughes, Organic Reactions 42 (1992) 335–656), for example by reaction with triphenylphosphine and DEAD in THF.

a2) The compound of the formula VI is reacted with a compound of the formula VII $$H-B-(CR^1R^2)_r-A'-(CR^1R^2)_s-(CR^1R^3)_k-(CR^1R^2)_t-R^{13} \quad (VII)$$

in which $R^{13}$ is $-D-E$ or a group $R^{14}$ which can be converted into D—E and which is optionally provided with suitable protective groups, and for which otherwise the above meanings apply. $R^{14}$ is, for example, an optionally protected amino group $-NHR^6$, it being possible to employ, for example, the Boc protective group as a protective group, a protected carboxylic acid ester, an aldehyde $-C(O)H$, a keto group $-C(O)R^6$, or a protected mercapto group.

In this reaction, a compound of the formula VIII (VIII)

is obtained, in which $R^{15}$ is $-B-(CR^1R^2)_r-A'-(CR^1R^2)_s-(CR^1R^3)_k-(CR^1R^2)_t-R^{13}$ and for which otherwise the above meanings apply.

The reaction is carried out according to methods known to those skilled in the art (see source literature in J. March, Advanced Organic Chemistry, Fourth Edition, Wiley, 1992), preferably in a suitable organic solvent or diluent, for example DCM, CHCl$_3$, THF, diethyl ether, n-heptane, n-hexane, n-pentane, cyclohexane, diisopropyl ether, methyl tert-butyl ether, acetonitrile, DMF, DMSO, dioxane, toluene, benzene, ethyl acetate or mixtures of these solvents, if appropriate with addition of a base such as, for example, butyllithium, lithium diisopropylamide (LDA), sodium hydride, sodium amide, potassium tert-butoxide, CaCO$_3$, Cs$_2$CO$_3$, triethylamine, diisopropylethylamine or complex bases (sodium amide/R$^{12}$ONa, where $R^{12}$ is (C$_2$–C$_6$)-alkyl or CH$_3$CH$_2$OCH$_2$CH$_2$), where for B=NR$^6$ an excess of VII can also serve as a base.

a3) If appropriate, the protective groups in the compound of the formula VIII on $R^{13}$ and/or $R^{10}$ are removed by known methods (Greene, Wuts, Protective Groups in Organic Synthesis, Wiley, 1991). If, for example, $R^{13}$ is a Boc-protected amino group, the Boc group can be removed, for example, by reaction with trifluoroacetic acid.

a4) If appropriate, $R^{13}$ in the compound of the formula VIII is then reacted according to known processes to give the group D—E, for example by one of the following processes.

a4.1) By reaction of compounds where $R^{13}=NHR^6$ with 1H-pyrazole-1-carboxamidine or cyanamide a guanidine is obtained (see Bernatowicz et al., J. Org. Chem. 57 (1992) 2497).

a4.2) By reaction of compounds where $R^{13}=NHR^6$ with a monocyclic system or polycyclic system of the type

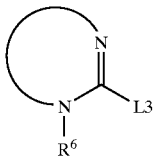

in which L3 is a nucleophilically substitutable leaving group such as, for example, halogen or SH, SCH$_3$, SOCH$_3$, SO$_2$CH$_3$ or HN—NO$_2$, compounds with the end group

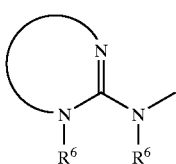

are obtained (for the process see, for example, A. F. McKay et al., J. Med. Chem. 6 (1963) 587; M. N. Buchman et al., J. Am. Chem. Soc. 71 (1949) 766; F. Jung et al., J. Med. Chem. 34 (1991) 1110; or G. Sorba et al., Eur. J. Med. Chem. 21 (1986), 391)

a4.3) By reaction of compounds where $R^{13}=NHR^6$ with compounds of the type

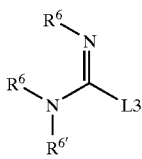

in which L3 is a nucleophilically substitutable leaving group such as, for example, halogen or SH, SCH$_3$, SOCH$_3$, SO$_2$CH$_3$ or HN—NO$_2$, compounds with the end group

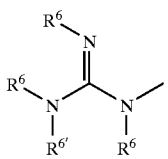

are obtained (for the process see, for example, Miller, Synthesis 1986, 777; or Brimble, J. Chem. Soc., Perkin Trans. 1 (1990) 311).

a4.4) By reaction of compounds where $R^{13}=NHR^6$ with a monocyclic or polycyclic system of the type

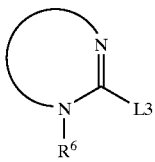

in which L3 is a nucleophilically substitutable leaving group such as, for example, SCH$_3$, compounds with the end group

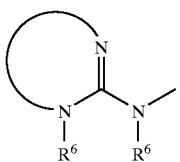

are obtained (for the process see, for example, T. Hiroki et al., Synthesis (1984) 703; or M. Purkayastha et al., Indian J. Chem. Sect. B 30 (1991) 646).

a 4.5) Compounds in which —D—E is the radical of an aminoguanidinylimine of the type

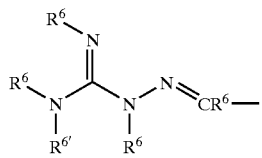

or of a cyclic aminoguanidinylimine of the type

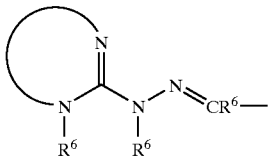

can be prepared, for example, by condensation of compounds of the formula

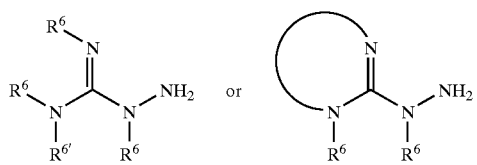

with ketones or aldehydes of the type O=C(R$^6$)— or corresponding acetals or ketals according to customary literature processes, for example analogously to N. Desideri et al., Arch. Pharm. 325 (1992) 773–777 or A. Alves et al., Eur. J. Med. Chem. Chim. Ther. 21 (1986) 297–304, where the above aminoguanidinylimines may be obtained as E/Z isomer mixtures which can be separated by customary chromatographic methods.

a4.6) Compounds in which —D—E is R$^6$—C(=NR$^6$)—NR$^6$—N=C(R$^6$)— or a radical containing a monocyclic system or a polycyclic system, of the type

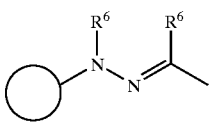

can be obtained analogously to a4.5).

a4.7) Compounds in which —D— is —S(O)$_2$NR$^6$— can be prepared, for example, by oxidizing compounds with $R^{13}$=SH to sulfonic acids ($R^{13}$=SO$_3$H) by methods known from the literature (cf. Houben-Weyl, Methoden der Organischen Chemie, Bd. E12/2, Georg Thieme Verlag, Stuttgart 1985, p. 1058ff), from which the compounds with —D—=—S(O)$_2$NR$^6$— are then prepared, for example, directly or via corresponding sulfonyl halides by linkage of an amide bond, where oxidation-sensitive groups in the molecule, such as, for example, amino groups, amidino groups or guanidino groups, are protected by suitable protective groups if necessary before carrying out the oxidation.

a4.8) Compounds in which —D— is —S(O)NR$^6$— can be prepared, for example, by converting compounds with R$^{13}$=SH into the corresponding sulfide and then oxidizing with meta-chloroperbenzoic acid to the sulfinic acids (R$^{13}$=SO$_2$H) (cf. Houben-Weyl, Methoden der Organischen Chemie, Vol. E11/1, Georg Thieme Verlag, Stuttgart 1985, p. 618f), from which the corresponding sulfinamides can be prepared according to methods known from the literature. Generally, other methods known from the literature can also be used for the preparation of compounds of the formulae I and Ia with —D——=—S(O)$_u$NR$^6$—(u=1, 2) (cf. Houben-Weyl, Methoden der Organischen Chemie, Vol. E11/1, Georg Thieme Verlag, Stuttgart 1985, p. 618ff or Vol. E11/2, Stuttgart 1985, p. 1055ff).

a4.9) Compounds in which —D—E is R$^6$R$^{6'}$N—C(=NR$^6$)—NR$^6$—C(O)— or the radical of a cyclic acylguanidine of the type

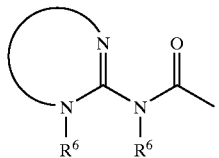

can be prepared, for example, by reacting a compound, in which R$^{13}$ is —C(O)—L4 and L4 is an easily nucleophilically substitutable leaving group, with the appropriate guanidine (derivative) of the type

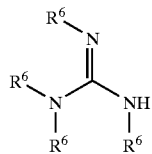

or the cyclic guanidine (derivative) of the type

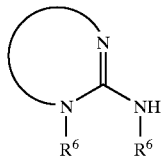

The activated acid derivatives with the group L4(O)C— indicated above, in which L4 can be, for example, an alkoxy group, preferably a methoxy group, a phenoxy group, phenylthio group, methylthio group, 2-pyridylthio group or a nitrogen heterocycle, preferably 1-imidazolyl, are advantageously obtained in a manner known per se from the carboxylic acid chlorides on which they are based (L4=Cl), which for their part can in turn be prepared in a manner known per se from the carboxylic acids on which they are based, for example using thionyl chloride. In addition to the carboxylic acid chlorides (L4=Cl) further activated acid derivatives with the group of the type L4(O)C— can also be prepared in a known manner directly from the carboxylic acids on which they are based (L4=OH), such as, for example, the methyl esters (L4=OCH$_3$) by treating with gaseous HCl in methanol, the imidazolides (L4=1-imidazolyl) by treating with carbonyldiimidazole (cf. Staab, Angew. Chem. Int. Ed. Engl. 1, 351–367 (1962)) or the mixed anhydrides (L4=C$_2$H$_5$OC(O)O or TosO) with Cl—COOC$_2$H$_5$ or tosyl chloride in the presence of triethylamine in an inert solvent. The activation of the carboxylic acids can also be carried out using carbodiimides like dicyclohexylcarbodiimide (DCCl) or using O-((cyano (ethoxycarbonyl)methylene)amino)-1,1,3,3-tetramethyluronium tetrafluoroborate ("TOTU") (König et al., Proc. 21st Europ. Peptide Symp. 1990, (Eds. Giralt, Andreu), Escom, Leiden, 1991; p. 143) and other activating reagents customary in peptide chemistry (a number of suitable methods for the preparation of activated carboxylic acid derivatives are given with source literature in J. March, Advanced Organic Chemistry, Third Edition (John Wiley & Sons, 1985), p. 350). The reaction of an activated carboxylic acid derivative having the group of the type L4(O)C— with the respective guanidine (derivative) is preferably carried out in a manner known per se in a protic or aprotic polar, inert organic solvent, the reaction of the methyl esters (L4=OMe) with the respective guanidines advantageously being carried out in methanol, isopropanol or THF at temperatures from 20° C. up to the boiling temperature of these solvents. Most reactions of compounds having the group L4(O)C— with salt-free guanidines are advantageously carried out in aprotic inert solvents such as THF, dimethoxyethane or dioxane, it also being possible, however, to use water as a solvent when using a base such as, for example, NaOH in the reaction of compounds having the group L4(O)C— with guanidines. If L4=Cl, the reaction is advantageously carried out with the addition of an acid scavenger, for example in the form of excess guanidine (derivative), for the binding of the hydrohalic acid.

a4.10) Compounds in which —D—E is R$^6$—C(=NR$^6$)—NR$^6$—C(O)— or a radical comprising a monocyclic system or polycyclic system, of the type

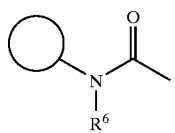

can be obtained analogously to a4.9).

a4.11) Compounds in which —D—E is the radical of a sulfonylguanidine or sulfoxylguanidine of the type R$^6$R$^{6'}$N—C(=NR$^6$)—NR$^6$—S(O)$_u$—(u=1, 2) or

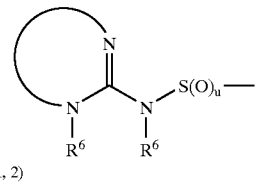

(u = 1, 2)

can be prepared by methods known from the literature by reaction of compounds of the formulae R$^6$R$^{6'}$N—C(=NR$^6$)—NHR$^6$ and

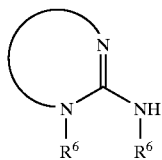

with compounds in which $R^{13}$ is $S(O)_u$—L5 (u=1, 2) and L5 is, for example, Cl or $NH_2$ for example analogously to S. Birtwell et al., J. Chem. Soc. (1946) 491 or Houben Weyl, Methoden der Organischen Chemie, Vol. E4, Georg Thieme Verlag, Stuttgart 1983; p. 620 ff.

a4.12) Compounds in which —D—E is $R^6$—C(=$NR^6$) $NR^6$—$S(O)_u$—(u=1, 2) or the radical comprising a monocyclic system or polycyclic system, of the type

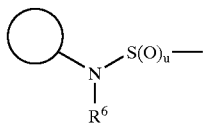

(u=1, 2), can be obtained analogously to a4.11).

a4.13) Compounds in which —D— is —$NR^6$—C(O)— can be prepared, for example, by first reacting a compound with $R^{13}$=—$NHR^6$ with a suitable carbonic acid derivative, preferably phosgene, diphosgene (trichloromethyl chloroformate), triphosgene (bis-trichloromethyl carbonate), ethyl chloroformate, i-butyl chloroformate, bis (1-hydroxy-1H-benzotriazolyl) carbonate or N,N'-carbonyidiimidazole, in a solvent which is inert to the reagents used, preferably DMF, THF or toluene, at temperatures between −20° C. and the boiling point of the solvent, preferably between 0° C. and 60° C., to give a compound in which $R^{13}$ is

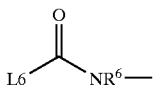

where L6, depending on the carbonic acid derivative used, is, for example, a hydroxyl group, halogen such as, for example, chlorine, ethoxy, isobutoxy, benzotriazol-1-oxy or 1-imidazolyl. The subsequent reaction of these derivatives with $R^6R^6$'N—C(=$NR^6$)—$NR^6$'H or $R^6$—C(=$NR^6$)—$NHR^6$ or with the compound comprising a monocyclic system or polycyclic system, of the type

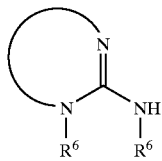 or 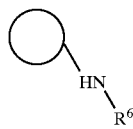

is then carried out as described above for the preparation of acylguanidines (or their derivatives) in a4.9).

a4.14) Compounds of the formula I in which —D—E is a bis-aminotriazole radical or a bis-aminooxadiazole radical can be prepared, for example, according to P. J. Garrett et al., Tetrahedron 49 (1993) 165 or R. Lee Webb et al., J. Heterocyclic Chem. 24 (1987) 275.

a4.15) Compounds of the formula I in which —D—E is a urea group or a thiourea group can be synthesized according to known methods, such as are summarized, for example, in C. Ferri, Reaktionen der organischen Synthese, Georg Thieme Veriag, Stuttgart 1978, for example by reaction of the corresponding amines with isocyanates or isothiocyanates.

a5) If appropriate, after the reaction of $R^{13}$ in the compound of the formula VIII to give the group D—E, further protective groups still to be removed are removed by known methods (see Greene, Wuts, see above).

a6) If appropriate, the compounds of the formula I obtained are converted into their salts, in particular into pharmaceutically utilizable or nontoxic, physiologically tolerable salts, and/or are converted into prodrugs.

The present invention furthermore also relates to processes for the synthesis of the compounds of the formula Ia, which comprise carrying out one or more of the following steps for the synthesis of the compounds of the formula Ia.

b1) A compound of the formula IV is reacted with a compound of the formula IX,

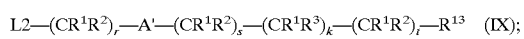

in which $R^1$, $R^2$, $R^3$, A', r, s, k, t, $R^{13}$ and L2 are as defined above, to give a compound of the formula X

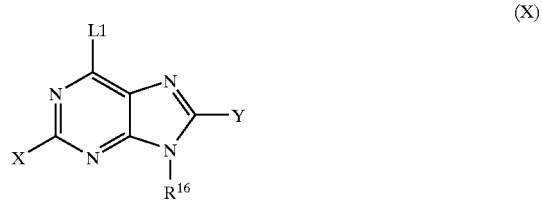

in which $R^{16}$ is —$(CR^1R^2)_r$—A'—$(CR^1R^2)_s$—$(CR^1R^3)_k$—$(CR^1R^2)_t$—$R^{13}$, L1, X and Y are as defined above and the meanings indicated above otherwise apply. The reaction is carried out by methods known to those skilled in the art (see source literature in J. March, Advanced Organic Chemistry, Fourth Edition, Wiley, 1992), preferably in a suitable organic solvent or diluent, for example DCM, $CHCl_3$, THF, diethyl ether, n-heptane, n-hexane, n-pentane, cyclohexane, diisopropyl ether, methyl tert-butyl ether, acetonitrile, DMF, DMSO, dioxane, toluene, benzene, ethyl acetate or mixtures of these solvents, if appropriate with addition of a base such as, for example, butyllithium, lithium diisopropylamide (LDA), sodium hydride, sodium amide, potassium tert-butoxide, $CaCO_3$, $Cs_2CO_3$, triethylamine, diisopropylethylamine or complex bases (sodium amide/$R^{12}$ONa, where $R^{12}$ is $(C_2\text{-}C_6)$-alkyl or $CH_3CH_2OCH_2CH_2$). For L2=OH, the reaction can be carried out, for example, by the conditions described for the Mitsunobu reaction (Hughes, Organic Reactions 42 (1992) 335–656), for example by reaction with triphenylphosphine and DEAD in THF.

b2) The compound of the formula X is reacted with a compound of the formula XI

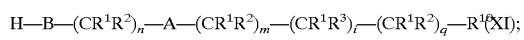

in which $R^1$, $R^2$, $R^3$, $R^{10}$, A, B, n, m, i and q are as defined above, to give a compound of the formula XII

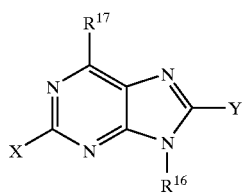

(XII)

in which $R^{16}$, X and Y are as defined above, $R^{17}$ is —B—$(CR^1R^2)_n$—A—$(CR^1R^2)_m$—$(CR^1R^3)_i$—$(CR^1R^2)_q$—$R^{10}$ and the meanings indicated above otherwise apply.

b3) For the further synthesis of compounds of the formula Ia, the procedure is then analogous to the steps a3) to a6) in the synthesis of the compounds of the formula I.

In the process for the synthesis of the compounds of the formula I, step a2) can also be carried out before a1). In the process for the synthesis of the compounds of the formula Ia, step b2) can also be carried out before b1).

The introduction of carbon substituents in the 6-position of the purine structure can be carried out, for example, by Stille coupling, such as described, for example, in Langli et al., Tetrahedron 52 (1996) 5625; Gundersen, Tetrahedron Lett. 35 (1994) 3153, or by Heck coupling, such as described, for example, in Koyama et al., Nucleic Acids Res., Symp. Ser. 11 (1982) 41.

A substituent X in position 2 of the purine structure can also be introduced by known methods at the end of the synthesis of the compounds of the formulae I and Ia, such as described, for example, in D. A. Nugiel, J. Org. Chem. 62 (1997) 201–203; N. S. Gray, Tetrahedron Lett. 38 (1997) 1161 and the references cited there.

A substituent representing Y in the 8-position can be introduced by known methods, such as described, for example, in E. J. Reist et al., J. Org. Chem. 33 (1968) 1600; J. L. Kelley et al., J. Med. Chem. 33 (1990) 196; or E. Vanotti et al., Eur. J. Chem. 29 (1994) 287.

The compounds of the formulae I and Ia according to the invention and their physiologically tolerable salts can be administered to animals, preferably to mammals, and in particular to humans as pharmaceuticals per se, in mixtures with one another or in the form of pharmaceutical preparations which permit enteral or parenteral use and which, as active constituent, contain an efficacious dose of at least one compound of the formula I or of the formula Ia or of a salt thereof or of a prodrug thereof in addition to customary pharmaceutically innocuous vehicles and/or additives. The pharmaceutical preparations normally contain approximately 0.5 to 90% by weight of the therapeutically active compounds.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example in the form of injection solutions or infusion solutions, microcapsules or rods, percutaneously, for example in the form of ointments or tinctures, or nasally, for example in the form of nasal sprays.

The pharmaceutical preparations are prepared in a manner known per se, pharmaceutically inert inorganic or organic vehicles being used. For the production of pills, tablets, coated tablets and hard gelatin capsules, it is possible to use, for example, lactose, corn starch or derivatives thereof, talc, stearic acid or its salts etc. Vehicles for soft gelatin capsules and suppositories are, for example, fats, waxes, semisolid and liquid polyols, natural or hardened oils, etc. Suitable vehicles for the production of solutions and syrups are, for example, water, sucrose, invert sugar, glucose, polyols, etc. Suitable vehicles for the production of injection solutions are water, alcohols, glycerol, polyols, vegetable oils, etc. Suitable vehicles for microcapsules, implants or rods are copolymers of glycolic acid and lactic acid.

In addition to the active compounds and vehicles, the pharmaceutical preparations can additionally contain additives, such as, for example, fillers, extenders, disintegrants, binders, lubricants, wetting agents, stabilizers, emulsifiers, preservatives, sweeteners, colorants, flavorings or aromatizers, thickeners, diluents, buffer substances, and also solvents or solubilizers or agents for achieving a depot effect, and also salts for altering the osmotic pressure, coating agents or antioxidants. They can also contain two or more compounds of the formula I or Ia and/or their physiologically tolerable salts, and also, in addition to at least one compound of the formula I or Ia or of a salt thereof, additionally one or more other therapeutically active substances.

The dose can vary within wide limits and is to be suited to the individual conditions in each individual case. In the case of oral administration, the daily dose is in general approximately 0.01 to 100 mg/kg, preferably 0.1 to 5 mg/kg, in particular 0.3 to 0.5 mg/kg, of body weight to achieve effective results. Also in the case of intravenous administration the daily dose is in general approximately 0.01 to 100 mg/kg, preferably 0.05 to 10 mg/kg, of body weight. The daily dose can be divided, in particular in the case of the administration of relatively large amounts, into several, for example 2, 3 or 4, part administrations. If appropriate, depending on the individual behavior, it may be necessary to deviate upwards or downwards from the daily dose indicated.

Apart from use as pharmaceutical active compounds, the compounds of the formulae I and Ia can also be employed for diagnostic purposes, for example in vitro diagnoses, and as tools in biochemical investigations in which inhibition of the vitronectin receptor or influencing of cell-cell or cell-matrix interactions is intended. Furthermore, they can be used as intermediates for the preparation of other compounds, in particular of other pharmaceutical active compounds, which are obtainable from the compounds of the formulae I and Ia, for example, by modification or introduction of residues or groups.

Abbreviations used:

| | |
|---|---|
| AcOH | acetic acid |
| Boc | tert-butoxycarbonyl |
| DCCI | dicyclohexylcarbodiimide |
| DCM | dichloromethane |
| DEAD | diethyl azodicarboxylate |
| DIPEA | diisopropylethylamine |
| DMF | dimethylformamide |
| DMSO | dimethyl sulfoxide |
| EA | ethyl acetate |
| HOOBt | 3-hydroxy-4-oxo-3,4-dihydro-1,2,3-benzotriazine |
| MeOH | methanol |
| Mes | methylsulfonyl |
| RT | room temperature |
| Tf | trifluoromethylsulfonyl |
| THF | tetrahydrofuran |
| Tos | p-toluenesulfonyl |
| Z | benzyloxycarbonyl |

EXAMPLES

Compounds of the formulae I and Ia which in the 6-position of the purine structure contain an amino group which is not a constituent of a ring can also be regarded as derivatives of adenine (=6-aminopurine) and can be designated as such in the nomenclature of the compounds. Substituents which are bonded to the nitrogen atom of the amino group in the 6-position of adenine are provided in this notation with the addendum $N^6$. Substituents which are bonded to the ring nitrogen atom in the 9-position are provided with the addendum $N^9$. In the name of the substituent it is indicated at the beginning via which position in the substituent the substituent is bonded to the nitrogen atom $N^6$ or $N^9$ in the chosen notation. The same applies to compounds which are designated as $N^9$-substituted derivatives of purine.

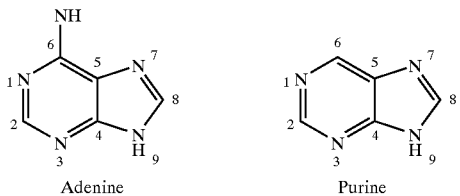

Adenine         Purine

Example 1

$N^6$-(1-(5-Guanidinopentyl))-$N^9$-(3-(2S-(benzyloxycarbonylamino)propionic acid))-adenine 1a) $N^9$-(3-(tert-Butyl 2S-(benzyloxycarbonylamino)propionate))-6-chloropurine 2.63 g (17 mmol) of 6-chloropurine and 4.46 g (16.5 mmol) of triphenylphosphine were suspended in 50 ml of absol. THF under argon. 2.56 ml (16.3 mmol) of DEAD were added at RT and the mixture was stirred at RT for 15 minutes, a clear solution being formed. 3.78 g (12.8 mmol) of N-benzyloxycarbonyl-L-serine tert-butyl ester (prepared according to M. Schultz, H. Kunz, Tetrahedron: Asymmetry 4 (1993) 1205–1220), dissolved in 50 ml of absol. THF, were added to this solution during the course of 1.5 h. The mixture was then stirred at RT for a further 2 h. The solvent was evaporated, and the residue was triturated with ether and chromatographed through silica gel (toluene:EA 98:2 to 7:3), 2.85 g (51%) of pure product being obtained.

$^1$H-NMR (200 MHz, DMSO): δ=1.30 (s, 9H, C(CH$_3$)$_3$); 4.48–4.73 (m, 3H, N$^9$—CH$_2$—CH(NHZ)); 4.98 (s, 2H, CH$_2$-aryl); 7.19–7.40 (m, 5H, aryl-H); 7.87 (d, 1H, NH); 8.61+8.77 (2 s, 2H, C$^6$—H+C$^8$—H). MS (FAB): m/e=432.1 (100%; (M+H)$^+$); 376.0 (60).

1b) $N^6$-(1-(5-(tert-Butyloxycarbonylamino)pentyl))-$N^9$-(3-(tert-butyl 2S-(benzyloxycarbonylamino)propionate))-adenine 0.170 ml (1 mmol) of DIPEA and 5 mg of potassium iodide were added to a solution of 431 mg (1 mmol) of $N^9$-(3-(tert-butyl 2S-(benzyloxycarbonylamino)propionate))-6-chloropurine (Example 1a) and 404 mg (2 mmol) of 5-(tert-butyloxycarbonylamino)-1-pentylamine in 5 ml of absol. DMF and the mixture was stirred at 40° C. for 72 h. The solvent was evaporated and the residue was chromatographed through silica gel (toluene:EA 7:3 to 1:2), 190 mg (32%) of pure product being obtained. MS (FAB): m/e=598.3 (100%; (M+H)$^+$).

1c) $N^6$-(1-(5-Aminopentyl))-$N^9$-(3-(2-(benzyloxycarbonylamino)propionic acid))-adenine 190 mg (0.32 mmol) of $N^6$-(1-(5-(tert-butyloxycarbonylamino)pentyl))-$N^9$-(3-(tert-butyl 2S-(benzyloxycarbonylamino)propionate))-adenine (Example 1b) were dissolved in 2 ml of 90% strength trifluoroacetic acid and the solution was stirred at RT for 2 h. It was evaporated to dryness and the residue was coevaporated twice with acetic acid. The residue was then dissolved in water and freeze-dried. Yield: 134 mg (95%). MS (ES+): m/e=442.3 (20%; (M+H)$^+$), 308.2 (35).

1d) $N^6$-(1-(5-Guanidinopentyl))-$N^9$-(3-(2S-(benzyloxycarbonylamino)propionic acid))-adenine 34 mg (0.077 mmol) of $N^6$-(1-(5-aminopentyl))-$N^9$-(3-(2S-(benzyloxycarbonylamino)propionic acid))-adenine (Example 1c) were dissolved in 1.5 ml of water and 0.5 ml of DMF and the solution was treated with 0.033 ml (0.193 mmol) of DIPEA and 13.5 mg (0.092 mmol) of 1H-pyrazole-1-carboxamidine hydrochloride and stirred at RT for 40 h. The solvent was then evaporated, the residue was taken up in water and the solution was freeze-dried. For further purification, it was chromatographed through silica gel (DCM:methanol:acetic acid:water 15:5:1:1). Yield: 70%. MS (FAB): m/e=484.2 (100%; (M+H)$^+$).

Example 2

$N^6$-(1-(4-Guanidinobutyl))-$N^9$-(3-(2S-(benzyloxycarbonylamino)propionic acid))-adenine 2a) $N^6$-(1-(4-(tert-Butyloxycarbonylamino)butyl))-$N^9$-(3-(tert-butyl 2S-(benzyloxycarbonylamino)propionate))-adenine Synthesis analogously to 1b from 431 mg (1 mmol) of $N^9$-(3-(tert-butyl 2S-(benzyloxycarbonylamino)propionate))-6-chloropurine (Example 1a) and 376 mg (2 mmol) of 4-(tert-butyloxycarbonylamino)-1 -butylamine. Yield: 214 mg (37%).

$^1$H-NMR (200 MHz, DMSO): δ=1.30 (s, 9H, C(CH$_3$)$_3$); 1.38 (s, 9H, C(CH$_3$)$_3$); 1.41 (m, 2H, CH$_2$); 1.57(m, 2H, CH$_2$); 3.46 (m, 2H, CH$_2$—NH-Boc); 2.92 (t, 2H, C$^2$—NH—CH$_2$); 4.31–4.58 (m, 3H, N$^1$—CH$_2$—CH(NHZ)); 5.01 (s, 2H, CH$_2$-aryl); 6.99 (t, 1H, C$^2$—NH); 7.10–7.38 (m, 5H, aryl-H); 7.75 (m, 1H, NH-Boc); 7.91 (d, 1H, NH—Z); 8.02+8.20 (2 s, 2H, C$^6$—H+C$^8$—H). MS (ES+): m/e=584.3 (100%; (M+H)$^+$).

2b) $N^6$-(1-(4-Aminobutyl))-$N^9$-(3-(2S-(benzyloxycarbonylamino)propionic acid))-adenine Synthesis analogously to Example 1c from $N^6$-(1 -(4-tert-butyloxycarbonylamino)butyl)-$N^9$-(3-(tert-butyl 2S-(benzyloxycarbonylamino)propionate)-adenine (Example 2a). Yield: 96%. MS (ES+): m/e=428.2 (100%; (M+H)$^+$), 294.1 (70).

2c) $N^6$-(1-(4-Guanidinobutyl))-$N^9$-(3-(2S-(benzyloxycarbonylamino)-propionic acid))-adenine Synthesis analogously to Example 1d from $N^6$-(1-(4-aminobutyl))-$N^9$-(3-(2S-(benzyloxycarbonylamino)propionic acid))-adenine (Example 2b). Yield: 76%. MS (ES+): m/e=470.1 (20%; (M+H)$^+$).

Example 3

$N^6$-(1-(3-Guanidinopropyl))-$N^9$-(3-(2S-(benzyloxycarbonylamino)propionic acid))-adenine 3a) $N^6$-(1-(3-(tert-Butyloxycarbonylamino)propyl))-$N^9$-(3-(tert-butyl 2S-(benzyloxycarbonylamino)propionate))-adenine Synthesis analogously to 1b from 60 mg (0.14 mmol) of $N^9$-(3-(tert-butyl 2S-(benzyloxycarbonylamino)propionate))-6-chloropurine (Example 1a) and 30 mg (0.17 mmol) of 3-(tert-butyloxycarbonylamino)-1-propylamine. Yield: 30 mg (38%).

$^1$H-NMR (200 MHz, DMSO): δ=1.28 (s, 9H, C(CH$_3$)$_3$); 1.36 (s, 9H, C(CH$_3$)$_3$); 1.68 (m, 2H, CH$_2$—CH$_2$—CH$_2$);

1.41 (m, 2H, $CH_2$); 2.98 (t, 2H, $C^2$—NH—$CH_2$); 3.46 (t, 2H, $CH_2$—NH-Boc); 4.29–4.59 (m, 3H, $N^1$—$CH_2$—CH (NHZ)); 5.00 (s, 2H, $CH_2$-aryl); 6.82 (t, 1H, $C^2$—NH); 7.21–7.40 (m, 5H, aryl-H); 7.72 (m, 1H, NH-Boc); 7.91 (d, 1H, NH—Z); 8.03+8.20 (2 s, 2H, $C^6$—H+$C^8$—H). MS (ES+): m/e=570.3 (100%; $(M+H)^+$).

3b) $N^6$-(1-(3-Aminopropyl))-$N^9$-(3-(2S-(benzyloxycarbonylamino)propionic acid))-adenine Synthesis analogously to Example 1c from $N^6$-(1-(3-(tert-butyloxycarbonylamino)propyl))-$N^9$-(3-(tert-butyl 2S-(benzyloxycarbonylamino)propionate))-adenine (Example 3a). Yield: 100%. MS (ES+): m/e=414.2 (100%; $(M+H)^+$), 280.1 (30).

3c) $N^6$-(1-(3-Guanidinopropyl))-$N^9$-(3-(2S-(benzyloxycarbonylamino)propionic acid))-adenine Synthesis analogously to Example 1d from $N^6$-(1-(3-aminopropyl))-$N^9$-(3-(2S-(benzyloxycarbonylamino) propionic acid))-adenine (Example 3b). Yield: 66%. MS (ES+): m/e=456.3 (20%; $(M+H)^+$), 130.1 (100).

Example 4

$N^6$-(1-(4-(4,5-Dihydro-1H-imidazol-2-ylamino) butyl))-$N^9$-(3-(2S-(benzyloxycarbonylamino) propionic acid))-adenine 153 mg (0.36 mmol) of $N^6$-(1-(4-aminobutyl))-$N^9$-(3-(2S-(benzyloxycarbonylaminno)propionic acid))-adenine (Example 2b) and 88 mg (0.36 mmol) of 2-(methylmercapto)-2-imidazoline hydroiodide were dissolved in 2 ml of water and the solution was adjusted to pH 9.0 using 1 N NaOH. It was stirred at 50° C. for 100 h. The solution was then brought to pH 1.5 using 1 N HCl, the solvent was evaporated and the residue was chromatographed several times through silica gel (DCM:MeOH 9:1 to 1:2, in each case using 0.1% AcOH, 0.1% $H_2O$), then DCM:MeOH:$H_2O$:AcOH 8:2:0.4:0.4. Yield: 7 mg (4%). MS (FAB): m/e=496.2 $(M+H)^+$, 100%); 518.2 ($M+Na^+$, 50).

Example 5

$N^6$-(1-(3-Guanidinopropyl))-$N^9$-(4-(2S-(benzyloxycarbonylamino)butyric acid))-adenine 5a) $N^9$-(4-(tert-Butyl 2S-(benzyloxycarbonylamino) butyrate))-6-chloropurine Synthesis analogously to Example 1a from 6-chloropurine and N-benzyloxycarbonyl-L-homoserine tert-butyl ester. Yield: 24%.

$^1$H-NMR (200 MHz, DMSO): δ=1.34 (s, 9H, $C(CH_3)_3$); 2.08–2.43 (m, 2H, N—$CH_2$—$CH_2$—CH); 3.81–3.93(m, 1H, CH—NHZ); 4.39 (t, 2H, $N^9$—$CH_2$); 5.02 (s, 2H, $CH_2$-aryl); 7.26–7.42 (m, 5H, aryl-H); 7.87 (d, 1H, NH); 8.63+8.75 (2 s, 2H, $C^6$—H+$C^8$—H). MS (FAB): m/e=446.1 (100%; $(M+H)^+$); 390.1 (65).

5b) $N^6$-(1-(3-(tert-Butyloxycarbonylamino)propyl))-$N^9$-(4-(tert-butyl 2S-(benzyloxycarbonylamino)butyrate))-adenine Synthesis analogously to 1b from 50 mg (0.11 mmol) of $N^9$-(4-(tert-butyl 2S-(benzyloxycarbonylamino)butyrate))-6-chloropurine (Example 5a) and 38 mg (0.22 mmol) of 3-(tert-butyloxycarbonylamino)-1-propylamine. Yield: 26 mg (41%). MS (ES+): m/e=584.3 (100%; $(M+H)^+$).

5c) $N^6$-(1-(3-Aminopropyl))-$N^9$-(4-(2-(benzyloxycarbonylamino)butyric acid))-adenine Synthesis analogously to Example 1c from $N^6$-(1-(3-(tert-butyloxycarbonylamino)propyl))-$N^9$-(4-(tert-butyl 2S-(benzyloxycarbonylamino)-butyrate))-adenine (Example 5b). Yield: 94%. MS (FAB): m/e=428.3 (100%; $(M+H)^+$).

5d) $N^6$-(1-(3-Guanidinopropyl))-$N^9$-(4-(2S-(benzyloxycarbonylamino)butyric acid))-adenine Synthesis analogously to Example 1d from $N^6$-(1-(3-aminopropyl))-$N^9$-(3-(2S-(benzyloxycarbonylamino) butyric acid))-adenine (Example 5c). Yield: 71%. MS (FAB): m/e=470.3 (70%; $(M+H)^+$).

5e) N-Benzyloxycarbonyl-L-homoserine 6 g (50.4 mmol) of L-homoserine were largely dissolved in 50 ml of DMF and treated at 0° C. in portions with 12.56 9 (50.4 mmol) of N-(benzyloxycarbonyloxy)succinimide. The mixture was stirred at 0° C. for 1 h, then at RT for 48 h. The solvent was distilled off and the residue was partitioned between EA and a saturated NaCl solution. The organic phase was washed with saturated NaCl solution, with 5% strength citric acid and again with saturated NaCl solution, dried, filtered and concentrated. The crystalline residue was stirred in ether, filtered off with suction, and washed with ether and pentane. Yield: 9.55 g (75%).

$^1$H-NMR (200 MHz, DMSO): δ=1.61–1.95 (m, 2H, $CH_2$—$CH_2$—OH); 3.42 (m, 2H, $CH_2$13 OH); 4.08 (m, 1H, CH—NH—Z); 4.57 (s, broad, 1H, OH); 5.02 (s, 2H, $CH_2$—Ph); 7.32 (m, 5H, aryl-H), 7.49 (d, 1H, NH—Z). MS (Cl+): m/e=236.1 ($M+H^+$—$H_2O$, 20%); 192.1 (50); 91.0 (100).

5f) N-Benzyloxycarbonyl-L-homoserine tert-butyl ester 3.8 g (15 mmol) of Z-L-homoserine and 3.42 g (15 mmol) of benzyltriethylammonium chloride were dissolved under argon in 110 ml of N-methyl-2-pyrrolidone and treated successively with 53.9 g (390 mmol) of $K_2CO_3$ and 98.7 g (720 mmol) of tert-butyl bromide. The solution was stirred at 55° C. for 22 h. The reaction mixture was poured into 1.5 l of ice water, extracted twice with toluene, and the organic phase was washed twice with saturated NaCl solution, dried, filtered and concentrated. The product was chromatographed through silica gel for further purification (n-heptane: EA 7:3 to 1:1). Yield: 2.0 g (43.1%).

$^1$H-NMR (200 MHz, $CDCl_3$): δ=1.45 (s, 9H, tBu); 1.51–1.74+2.03–2.26 (m, 2H, $CH_2$—$CH_2$—OH); 3.01 (s, broad, 1H, OH); 3.70 (m, 2H, $CH_2$—OH); 4.41 (m, 1H, CH—NH—Z); 5.12 (s, 2H, $CH_2$—Ph); 5.60 (d, 1H, NH—Z); 7.36 (m, 5H, aryl-H),. MS (Cl+): m/e=310.3 ($M+H^+$, 50%); 254.2 (100).

Example 6

$N^6$-(1-(4-Guanidinobutyl))-$N^9$-(4-(2S-(benzyloxycarbonylamino)butyric acid))-adenine 6a) $N^6$-(1-(4-(tert-Butyloxycarbonylamino)butyl)-$N^9$-(4-(tert-butyl 2S-(benzyloxycarbonylamino)butyrate))-adenine Synthesis analogously to 1b from 50 mg (0.11 mmol) of $N^9$-(4-(tert-Butyl 2S-(benzyloxycarbonylamino)butyrate))-6-chloropurine (Example 5a) and 41 mg (0.22 mmol) of 4-(tert-butyloxycarbonylamino)-1-butylamine. Yield: 38 mg (58%). MS (ES+): m/e=598.3 (100%; $(M+H)^+$).

6b) $N^6$-(1-(4-Aminobutyl))-$N^9$-(4-(2-(benzyloxycarbonylamino)butyric acid))-adenine Synthesis analogously to Example 1 c from $N^6$-(1 -(4-(tert-butyloxycarbonylamino)butyl))-$N^9$-(4-(tert-butyl 2S-(benzyloxycarbonylamino)-butyrate))-adenine (Example 6a). Yield: 100%. MS (FAB): m/e=442.3 (100%; $(M+H)^+$).

6c) $N^6$-(1-(4-Guanidinobutyl))-$N^9$-(4-(2S-(benzyloxycarbonylamino)butyric acid))-adenine Synthesis analogously to Example 1d from $N^6$-(1-(4-aminobutyl))-$N^9$-(3-(2S-(benzyloxycarbonylamino)butyric acid))-adenine (Example 6b). Yield: 65%. MS (ES+): m/e= 484.3 (5%; $(M+H)^+$), 350.2 (10), 333.2 (5), 130.0 (100).

Example 7

N⁶-(1-(3-Guanidinopropyl))-N⁹-(3-propionic acid)-adenine

7a) N⁹-(tert-butyl 3-propionate)-6-chloropurine 15.45 g (0.1 mol) of 6-chloropurine, 43.5 ml (0.3 mol) of tert-butyl acrylate and 1.34 ml (7 mmol) of 5.22 N sodium methoxide (in MeOH) were dissolved in 400 ml of absol. MeOH and boiled under reflux for 4.5 h with repeated addition of 2.6 ml (14 mmol) of 5.22 N sodium methoxide (in MeOH). For working-up, the solid was filtered off with suction, the solvent was evaporated and the residue was chromatographed (toluene:EA 3:1) through silica gel (+10% $H_2O$). Yield: 1.35 g (5%).

$^1$H-NMR (200 MHz, DMSO): δ=1.29 (s, 9H, $C(CH_3)_3$); 2.95 (t, 2H, $CH_2C(O)$); 4.50 (t, 2H, N—$CH_2$); 8.70+8.79 (2 s, 2H, $C^6$—H+$C^8$—H). MS (ES+): m/e=283.1 (70%; $(M+H)^+$); 227.0 (100).

7b) N⁶-(1-(3-(tert-Butyloxycarbonylamino)propyl))-N⁹-(tert-butyl 3-propionate)-adenine Synthesis analogously to 1b from 282 mg (1.0 mmol) of N⁹-(tert-butyl 3-propionate)-6-chloropurine (Example 7a) and 209 mg (1.2 mmol) of 3-(tert-butyloxycarbonylamino)-1-propylamine. Yield: 160 mg (38%). MS (ES+): m/e=421.2 (100%; $(M+H)^+$), 365.2 (60), 321.2 (50), 265.1 (30).

7c) N⁶-(1-(3-Aminopropyl))-N⁹-(3-propionic acid)-adenine

Synthesis analogously to Example 1c from N⁶-(1-(3-(tert-butyloxycarbonylamino)propyl))-N⁹-(tert-butyl 3-propionate)-adenine (Example 7b). Yield: 100%.

$^1$H-NMR (200 MHz, DMSO): δ=1.88 (t, 2H, $CH_2$—$CH_2$—$CH_2$—); 2.80–2.93 (m, 4H, NH—$CH_2$+$CH_2$—C(O)); 3.56 (m, 2H, $CH_2$—$NH_2$); 4.38 (t, 2H, N⁹—$CH_2$); 7.72 (s, broad, 2H, $NH_2$); 7.95 (t, 1H, NH); 8.15+8.23 (2 s, 2H, $C^6$—H+$C^8$—H). MS (ES+): m/e=265.1 (100%; $(M+H)^+$); 248.1 (40), 176.0 (30).

7d) N⁶-(1-(3-Guanidinopropyl))-N⁹-(3-propionic acid)-adenine

Synthesis analogously to Example 1d from N⁶-(1-(3-aminopropyl))-N⁹-(3-propionic acid)-adenine (Example 7c). Yield: 41%.

$^1$H-NMR (200 MHz, $D_2O$): δ=1.95 (t, 2H, $CH_2$—$CH_2$—$CH_2$—); 2.71 (t, 2H, $CH_2$—C(O)); 3.24 (t, 2H, Gua—$CH_2$); 3.65 (m, 2H, $CH_2$—$NH_2$); 4.40 (t, 2H, N⁹—$CH_2$); 8.00+8.15 (2 s, 2H, $C^6$—H+$C^8$—H). MS (ES+): m/e=307.1 (100%; $(M+H)^+$), 290.1 (30).

Example 8

N⁶-(1-(4-Guanidinobutyl))-N⁹-(3-propionic acid)-adenine

8a) N⁶-(4-(tert-Butyloxycarbonylamino)butyl))-N⁹-(tert-butyl 3-propionate)-adenine Synthesis analogously to 1b from 141 mg (0.5 mmol) of N⁹-(tert-butyl 3-propionate)-6-chloropurine (Example 7a) and 104 mg (0.55 mmol) of 4-(tert-butyloxycarbonylamino)-1-butylamine. Yield: 130 mg (60%).

$^1$H-NMR (200 MHz, DMSO): δ=1.32 (s, 9H, $C(CH_3)_3$); 1.35 (s, 9H, $C(CH_3)_3$); 1.40 (t, 2H, $CH_2$); 1.57 (t, 2H, $CH_2$); 2.84 (t, 2H, —$CH_2$—C(O)); 2.95 (t, 2H, $C^2$—NH—$CH_2$); 3.45 (m, 2H, $CH_2$—NH-Boc); 4.34 (t, 2H, N⁹—$CH_2$); 6.78 (t, 1H, $C^2$—NH); 7.70 (m, 1H, NH-Boc); 8.08+8.19 (2 s, 2H, $C^6$—H+$C^8$—H). MS (ES+): m/e=435.2 (100%; $(M+H)^+$), 379.2 (20), 335.2 (55), 279.1 (50).

8b) N⁶-(1-(4-Aminobutyl))-N⁹-(3-propionic acid)-adenine

Synthesis analogously to Example 1c from N⁶-(1-(4-(tert-butyloxycarbonylamino)butyl)-N⁹-(tert-butyl 3-propionate)-adenine (Example 8a). Yield: 100%.

$^1$H-NMR (200 MHz, DMSO): δ=1.50–1.70 (m, 4H, —$CH_2$—$CH_2$—); 2.74–2.91 (m, 4H, NH—$CH_2$+$CH_2$—C(O)); 3.50 (m, 2H, $CH_2$—$NH_2$); 4.36 (t, 2H, N⁹—$CH_2$); 7.64 (s, broad, 2H, $NH_2$); 7.90 (t, 1H, NH); 8.11+8.21 (2 s, 2H, $C^6$—H+$C^8$—H). MS (FAB): m/e=279.2 (100%; $(M+H)^+$).

8c) N⁶-(1-(4-Guanidinobutyl))-N⁹-(3-propionic acid)-adenine

Synthesis analogously to Example 1d from N⁶-(1-(4-aminobutyl))-N⁹-(3-propionic acid)-adenine (Example 8b). Yield: 65%. MS (ES+): m/e=321.1 (100%; $(M+H)^+$).

Example 9

N⁶-(1-(5-Guanidinopentyl))-N⁹-(3-propionic acid)-adenine

9a) N⁶-(1-(5-(tert-Butyloxycarbonylamino)butyl))-N⁹-(tert-butyl 3-propionate)-adenine Synthesis analogously to 1b from 282 mg (1.0 mmol) of N⁹-(tert-butyl 3-propionate)-6chloropurine (Example 7a) and 243 mg (1.2 mmol) of 5-(tert-butyloxycarbonylamino)-1-pentylamine. Yield: 219 mg (41%). MS (ES+): m/e=449.3 (100%; $(M+H)^+$).

9b) N⁶-(1-(5-Aminopentyl))-N⁹-(3-propionic acid)-adenine

Synthesis analogously to Example 1c from N⁶-(1-(5-(tert-butyloxycarbonylamino)pentyl))-N⁹-(tert-butyl 3-propionate)-adenine (Example 9a). Yield: 100%.

$^1$H-NMR (200 MHz, DMSO): δ=1.39 (m, 2H, $CH_2$) 1.50–1.67 (m, 4H, 2×$CH_2$); 2.79 (dt, 2H, NH—$CH_2$); 2.89 (m, 2H, $CH_2$—C(O)); 3.48 (m, 2H, $CH_2$—$NH_2$); 4.37 (t, 2H, N⁹—$CH_2$); 7.67 (s, broad, 2H, $NH_2$); 8.04 (t, 1H, NH); 8.13+8.25 (2 s, 2H, $C^6$—H+$C^8$—H). MS (ES+): m/e=293.1 (100%; $(M+H)^+$).

9c) N⁶-(1-(5-Guanidinopentyl))-N⁹-(3-propionic acid)-adenine

Synthesis analogously to Example 1d from N⁶-(1-(5-aminopentyl))-N⁹-(3-propionic acid)-adenine (Example 9b). Yield: 37%.

$^1$H-NMR (200 MHz, DMSO): δ=1.38–1.79 (m, 6H, 3×$CH_2$); 2.80 (t, 2H, NH—$CH_2$); 3.12 (m, 2H, $CH_2$—C(O)); 3.58 (m, 2H, $CH_2$—Gua); 4.43 (t, 2H, N⁹—$CH_2$); 8.07+8.21 (2 s, 2H, $C^6$—H+$C^8$—H). MS (FAB): m/e=335.2 (100%; $(M+H)^+$).

Example 10

N⁶-(2-Acetic acid)-N⁹-(1-(5-aminopentyl))-adenine

10a) N⁶-(tert-Butyl 2-acetate)-adenine 155 mg (1 mmol) of 6-chloropurine and 420 mg (2 mmol) of glycine tert-butyl ester hydrochloride (80% strength) were dissolved in 5 ml of absol. DMF and treated with 0.17 ml of DIPEA and a spatula tipful of potassium iodide and the mixture was stirred at 50° C. for 6 h. The solvent was evaporated and the residue was chromatographed through silica gel (toluene:EA 1:1 to 1:2). Yield: 76 mg (31%) MS (ES+): 250.0 (M+H, 10%); 193.9 (95), 163.9 (100).

10b) N⁶-(2-Acetic acid)-N⁹-(1-(5-(tert-butyloxycarbonylamino)pentyl))-adenine 75 mg (0.3 mmol) of N⁶-(tert-butyl 2-acetate)-adenine (Example 10a), 214 mg (0.6 mmol) of 5-(tert-butyloxycarbonylamino)pentyl 4-toluene-sulfonate) and 42 mg (0.3 mmol) of $K_2CO_3$ were dissolved in 6 ml of absol. DMF and the solution was stirred at RT for 5 days. The solvent was evaporated and the residue was chromatographed through silica gel (toluene:EA 7:3 to 1:2). Yield: 92 mg (71%). MS (ES+): 435.3 (M+H, 25%); 349.3 (100).

10c) N⁶-(2-Acetic acid)-N⁹-(1-(5-aminopentyl))-adenine

Synthesis analogously to Example 1c from N⁶-(2-acetic acid)-N⁹-(1-(5-(tert-butyloxycarbonylamino)pentyl))- adenine (Example 10b). Yield: 93%. MS (ES+): m/e=279.2 (15%; (M+H)$^+$, 249.1 (100).

Example 11

N$^6$-(2-(N-(2-Aminoethyl)acetamide))-N$^9$-(2-acetic acid)-adenine

11a) N$^9$-(tert-butyl 2-acetate)-adenine 6.76 g (0.05 mol) of -adenine were suspended in 300 ml of absol. DMF under N$_2$, then 2.4 g (0.06 mol) of NaH dispersion were added and the mixture was stirred at RT for 2 h. 14.7 ml (0.1 mol) of tert-butyl bromoacetate were added dropwise in the course of 30 min, a clear solution being formed. It was stirred at RT for a further 5 h. The solvent was evaporated, the residue was stirred with 500 ml of water, and the solid was filtered off with suction and crystallized from ethanol. Yield: 5.1 9 (41%).

$^1$H-NMR (200 MHz, DMSO): δ=1.42 (s, 9H, tBu); 4.95 (s, 2H, N$^9$—CH$_2$); 7.22 (s, broad, 2H, N$^6$H$_2$); 8.10+8.15 (2 s, 2H, C$^6$—H+C$^8$—H). MS (ES+): m/e=250.1 (M+H$^+$, 65%), 194.0 (100).

11b) N$^6$-(ethyl 2-acetate)-N$^9$-(tert-butyl 2-acetate)-adenine 978 mg (3 mmol) of NaH and 250 mg (1 mmol) of N$^9$-(tert-butyl 2-acetate)-adenine (Example 11a) were suspended in 10 ml of absol. DMF and 0.12 ml of ethyl chloroacetate was added dropwise during the course of 10 min. The mixture was then stirred at 50° C. for 6 h, then the same amount of CsCO$_3$ was added again and the mixture was stirred at 50° C. for 6 h. The solvent was evaporated and the residue was partitioned between water and EA. The organic phase was dried and concentrated. Yield: 16%.

$^1$H-NMR (200 MHz, DMSO): δ=1.20 (t, 3H, CH$_2$—CH$_3$); 1.41 (s, 9H, tBu); 4.00–4.28 (m, 4H, CH$_2$—CH$_3$+N$^6$—CH$_2$); 4.98 (s, 2H, N$^9$—CH$_2$); 8.09 (s, broad, 1H, N$^6$H); 8.15+8.21 (2 s, 2H, C$^6$—H+C$^8$—H). MS (ES+): m/e=336.3 (M+H$^+$, 100%); 280.3 (60).

11c) N$^6$-(2-Acetic acid)-N$^9$-(tert-butyl 2-acetate)-adenine 249 mg (0.74 mmol) of N$^6$-(ethyl 2-acetate)-N$^9$-(tert-butyl 2-acetate)-adenine (Example 11b) were dissolved in 6 ml of dioxane:water:triethylamine and stirred at RT for 4 days. The solvent was evaporated and the residue was chromatographed through silica gel (DCM:MeOH 95:5 to 90:10). Yield: 36%. MS (ES+): m/e 308.3 (M+H$^+$, 100%).

11d) N$^6$-(2-(N-(2-tert-Butyloxycarbonylaminoethyl) acetamide))-N$^9$-(tert-butyl 2-acetate)-adenine 80 mg (0.26 mmol) of N$^6$-(2-acetic acid)-N$^9$-(tert-butyl 2-acetate)-adenine (Example 11c), 42 mg (0.26 mmol) of 2-tert-butyloxycarbonylaminoethylamine were dissolved in 5 ml of absol. DMF under argon and the mixture was treated at 0° C. with 85 mg (0.26 mmol) of TOTU and 0.13 ml (0.78 mmol) of DIPEA and stirred at 0° C. for 10 min and at RT for 2.5 h. It was diluted to 100 ml using EA, then washed with saturated potassium hydrogencarbonate solution, dried and concentrated. It was chromatographed through silica gel (DCM:MeOH 98:2 to 90:10). Yield: 5%. MS (ES+): m/e= 450.3 (M+H$^+$, 100%).

11e) N$^6$-(2-(N-(2-Aminoethyl)acetamide))-N$^9$-(2-acetic acid)-adenine

Synthesis analogously to Example 1c from N$^6$-(2-(N-(2-tert-butyloxycarbonylaminoethyl)acetamide))-N$^9$-(tert-butyl 2-acetate)-adenine (Example 11d). Yield: 80%. MS (ES+): m/e 293.1 (100%; (M+H)$^+$).

Example 12

N$^6$-(4-(2S-(Benzyloxycarbonylamino)butyric acid))-N$^9$-(1-(3-guanidinylpropyl))-adenine 12a) N$^9$-(1-(3-(tert-Butyloxycarbonylamino)propyl))-6-chloropurine 154.6 mg (1 mmol) of 6-chloropurine were dissolved in 2.5 ml of absol. DMF and treated with stirring with 331.7 mg (2.4 mmol) of K$_2$CO$_3$ and 285.8 mg (1.2 mmol) of tert-butyl N-(3-bromopropyl)carbamate. The mixture was stirred at RT for 11 h, the solvent was evaporated, the residue was taken up in EA and the solution was washed twice with saturated NaHCO$_3$ solution, then with NaCl solution, dried, filtered and concentrated. The residue was chromatographed through silica gel (EA:n-heptane 8:2). Yield: 267 mg (86%).

$^1$H-NMR (200 MHz, DMSO): δ=1.37 (s, 9H, tBu); 2.00 (tt, 2H, CH$_2$—CH$_2$—CH$_2$); 2.95 (dt, 2H, CH$_2$—NH); 4.30 (t, 2H, N$^9$—CH$_2$); 6.91 (t, broad, 1H, NH); 8.70+8.78 (2 s, 2H, C$^6$—H+C$^8$—H). MS (ES+): m/e=312.2 (100%; (M+H)$^+$); 256.1 (20).

12b) N$^6$-(4-(2S-(Benzyloxycarbonylamino)butyric acid))-N$^9$-(1-(3-(tert-butyloxy-carbonylamino)propyl))-adenine 370 mg (1.19 mmol) of N$^9$-(1-(3-(tert-butyloxycarbonylamino)propyl))-6-chloropurine (Example 12a) were dissolved in 10 ml of absol. DMF and 5 ml of DIPEA. 449 mg (1.8 mmol) of 2S-benzyloxycarbonylamino-4-aminobutyric acid were added at RT and the mixture was stirred at 65° C. for 50 h. The solvent was evaporated and the residue was partitioned between EA and saturated NaCl solution (20% KHSO$_4$). The organic phase was washed with water, dried, filtered and concentrated. The residue was chromatographed through silica gel (EA:MeOH 8:2). Yield: 331 mg (53%).

$^1$H-NMR (200 MHz, DMSO): δ=1.39 (s, 9H, tBu); 1.73–2.21 (m, 2H, CH$_2$—CH(NH—Z)); 1.90 (m, 2H, CH$_2$—CH$_2$-CH$_2$); 2.92 (dt, 2H, CH$_2$—NHBoc); 3.15 (dt, 2H, N$^6$H—CH$_2$); 3.88–4.10 (m, 1H, CH—NHZ); 4.14 (t, 2H, N$^9$-CH$_2$); 5.03 (s, 2H, CH$_2$—Ph); 6.91 (t, broad, 1H, NH-Boc); 7.37 (s, 5H, Ar—H); 7.55–7.81 (m, 2H, NH—Z+N$^6$H—CH$_2$); 8.13+8.19 (2 s, 2H, C$^6$—H+C$^8$—H). MS (ES+): m/e=528.2 (100%; (M+H)$^+$).

12c) N$^6$-(4-(2S-(Benzyloxycarbonylamino)butyric acid))-N$^9$-(1-(3-aminopropyl))-adenine 30 mg (0.06 mmol) of N$^6$-(3-(2S-(benzyloxycarbonylamino)propionic acid))-N$^9$-(1-(3-(tert-butyloxycarbonylamino)propyl))-adenine (Example 12b) were dissolved in 2 ml of 90% strength trifluoroacetic acid, the solution was stirred at RT for 70 min and concentrated, and the residue was stirred several times with ether. The residue was then dissolved in water, and the solution was freeze-dried. Yield: 100%. MS (ES+): m/e=428.2 (100%; (M+H)$^+$); 294.1 (90).

12d) N$^6$-(4-(2S-(Benzyloxycarbonylamino)butyric acid))-N$^9$-(1-(3-guanidinylpropyl))-adenine Synthesis analogously to Example 1d from N$^6$-(3-(2S-(benzyloxycarbonylamino)propionic acid))-N$^9$-(1-(3-aminopropyl))-adenine (Example 12c). Yield: 77%. MS (ES+): m/e=470.3 (25%; (M+H)$^+$); 336.2 (100).

Example 13

N$^6$-(4-(2S-(Benzyloxycarbonylamino)butyric acid))-N$^9$-(1-(3-(4,5-dihydro-1H-imidazol-2-ylamino) propyl))-adenine Synthesis analogously to Example 4 from N$^6$-(3-(2S-(benzyloxycarbonylamino)propionic acid))-N$^9$-(1-(3-aminopropyl))-adenine (Example 12c). Yield: 63%. MS (ES+): m/e=496.3 (100%; (M+H)$^+$).

Example 14

N$^6$-(3-(2S-(Benzyloxycarbonylamino)propionic acid))-N$^9$-(1-(5-guanidinyl-pentyl))-adenine 14a) N$^9$-(1-(5-(tert-Butyloxycarbonylamino)pentyl))-6-chloropurine Synthesis analogously to Example 12a from 6-chloropurine and tert-butyl N-(5-tosyloxypentyl) carbamate. Yield: 66%.

$^1$H-NMR (200 MHz, DMSO): δ=1.11–1.48 (m, 4H, 2×CH$_2$); 1.35 (s, 9H, tBu); 1.87 (tt, 2H, CH$_2$); 2.97 (dt, 2H, CH$_2$—NHBoc); 4.28 (t, 2H, N$^9$—CH$_2$); 6.72 (t, broad, 1H, NH); 8.71+8.78 (2 s, 2H, C$^6$—H+C$^8$—H). MS (ES+): m/e=340.2 (100%; (M+H)$^+$); 284.1 (50).

14b) N$^6$-(3-(2S-(Benzyloxycarbonylamino)propionic acid))-N$^9$-(1-(5-(tert-butyloxycarbonylamino)pentyl))-adenine Synthesis analogously to Example 12b from N$^9$-(1-(5-(tert-butyloxycarbonylamino)pentyl))-6-chloropurine and 2S-benzyloxycarbonylamino-3-aminopropionic acid. Yield: 23%.

$^1$H-NMR (200 MHz, DMSO): δ=1.10–1.49 (m, 4H, 2×CH$_2$; 1.36 (s, 9H, tBu); 1.62–1.88 (m, 2H, CH$_2$); 2.87 (dt(2H, CH$_2$—NHBoc); 3.68–4.98 (m, 5H, N$^9$—CH$_2$+CH$_2$—CH—NHZ); 5.00 (s, 2H, CH$_2$—Ph); 6.75 (t, broad, 1H, NH); 8.02+8.20 (2 s, 2H, C$^6$—H+C$^8$—H). MS (FAB): m/e=542.3 (100%; (M+H)$^+$).

14c) N$^6$-(3-(2S-(Benzyloxycarbonylamino)propionic acid))-N$^9$-(1-(5-amino-pentyl))-adenine Synthesis analogously to Example 12c from N$^6$-(3-(2S-(benzyloxycarbonylamino)propionic acid))-N$^9$-(1-(5-(tert-butyloxycarbonylamino)-pentyl))-adenine (Example 14b). Yield: 100%.

$^1$H-NMR (200 MHz, DMSO): δ=1.18–1.40+1.44–1.65+1.71–1.93 (2 m, 6H, 3×CH$_2$); 2.77 (dt(2H, CH$_2$—NHBoc); 3.64–4.35 (m, 5H, N$^9$—CH$_2$+CH$_2$CH—NHZ); 5.00 (s, 2H, CH$_2$—Ph); 7.66 (m, 3H, NH$_3^+$); 8.20+8.24 (2 s, 2H, C$^6$—H+C$^8$—H). MS (ES+): m/e=442.3 (40%; (M+H)$^+$); 308.2 (100).

14d) N$^6$-(3-(2S-(Benzyloxycarbonylamino)propionic acid))-N$^9$-(1-(5-guanidinylpentyl))-adenine Synthesis analogously to Example 1d from N$^6$-(3-(2S-(benzyloxycarbonylamino)propionic acid))-N$^9$-(1-(5-aminopentyl))-adenine (Example 14c). Yield: 90%. MS (ES+): m/e=484.3 (70%; (M+H)$^+$); 350.2 (60).

Example 15

N$^6$-(3-(2S-(Benzyloxycarbonylamino)propionic acid))-N$^9$-(1-(5-(4,5-dihydro-1H-imidazol-2-ylamino)pentyl))-adenine Synthesis analogously to Example 4 from N$^6$-(3-(2S-(benzyloxycarbonylamino)propionic acid)-N$^9$-(1-(5-aminopentyl))-adenine (Example 14c). Yield: 75%. MS (ES+): m/e 510.3 (40%; (M+H)$^+$); 376.2 (100).

Example 16

N$^6$-(3-(2S-(Benzyloxycarbonylamino)propionic acid))-N$^9$-(1-(3-guanidinylpropyl))-adenine 16a) N$^6$-(3-(2S-(Benzyloxycarbonylamino)propionic acid))-N$^9$-(1-(3-(tert-butyloxycarbonylamino)propyl))-adenine Synthesis analogously to Example 12b from N$^9$-(1-(3-(tert-butyloxycarbonylamino)propyl))-6-chloropurine (Example 12a) and 2S-benzylocarbonylamino-3-aminopropionic acid. Yield: 27%.

$^1$H-NMR (200 MHz, DMSO): δ=1.37 (s, 9H, tBu); 1.90 (m, 2H, CH$_2$—CH$_2$—CH$_2$); 2.92 (dt, 2H, CH$_2$—NHBoc); 3.86 (m, broad, 2H, CH$_2$—CH(NH—Z)); 4.13 (t, 2H, N$^9$—CH$_2$); 4.40 (m, 1H, CH—NHZ); 5.01 (s, 2H, CH$_2$—Ph); 6.92 (t, broad, 1H, NH-Boc); 7.33 (s, 5H, Ar—H); 7.55–7.75 (m, 2H, NH—Z+N$^6$H—CH$_2$); 8.16+8.22 (2 s, 2H, C$^6$—H+C$^8$—H). MS (ES+): m/e=514.3 (100%; (M+H)$^+$).

16b) N$^6$-(3-(2S-(Benzyloxycarbonylamino)propionic acid))-N$^9$-(1-(3-amino-propyl))-adenine Synthesis analogously to Example 12c from N$^6$-(3-(2S-(benzyloxycarbonylamino)propionic acid))-N$^9$-(1-(3-(tert-butyloxycarbonylamino)-propyl))-adenine (Example 16a). Yield: 100%. MS (ES+): m/e=414.2 (100%; (M+H)$^+$); 280.2 (70).

16c) N$^6$-(3-(2S-(Benzyloxycarbonylamino)propionic acid))-N$^9$-(1-(3-guanidinylpropyl))-adenine Synthesis analogously to Example 1d from N$^6$-(3-(2S-(benzyloxycarbonylamino)propionic acid))-N$^9$-(1-(3-aminopropyl))-adenine (Example 16b). Yield: 98%. MS (ES+): m/e=456.3 (40%; (M+H)$^+$); 322.2 (100).

Example 17

N$^6$-(3-(2S-(Benzyloxycarbonylamino)propionic acid))-$^9$-(1-(4guanidinyl-butyl))-adenine 17a) N$^9$-(1-(4-tert-Butyloxycarbonylamino)butyl))-6-chloropurine Synthesis analogously to Example 12a from 6-chloropurine and tert-butyl N-(4-tosyloxybutyl) carbamate. Yield: 66%.

$^1$H-NMR (200 MHz, DMSO): δ=1.30 (m, 2H, CH$_2$); 1.35 (s, 9H, tBu); 1.86 (tt, 2H, CH$_2$); 2.93 (dt, 2H, CH$_2$—NHBoc); 4.31 (t, 2H, N$^2$—CH$_2$); 6.79 (t, broad, $_1$H, NH) 8.72+8.78 (2 s, 2H, C$^6$—H+C$^8$—H). MS (ES+): m/e=326.2 (80%; (M+H)$^+$); 270.1 (100).

17b) N$^6$-(3-(2S-(Benzyloxycarbonylamino)propionic acid))-N$^9$-(1-(4-(tert-butyloxycarbonylamino)butyl))-adenine Synthesis analogously to Example 12b from N$^9$-(1-(4-tert-butyloxycarbonylamino)butyl))-6-chloropurine (Example 17a) and 2S-benzyloxycarbonylamino-3-aminopropionic acid. Yield: 33%.

$^1$H-NMR (200 MHz, DMSO): δ=1.30 (m, 2H, CH$_2$); 1.35 (s, 9H, tBu); 1.75 (m, 2H, CH$_2$); 2.91 (dt(2H, CH$_2$—NHBoc); 3.71–4.34 (m, 5H, CH$_2$—CH(NH—Z)+N$^9$—CH$_2$); 5.01 (s, 2H, CH$_2$—Ph); 6.89 (t, broad, 1H, NH-Boc); 7.35 (s, 5H, Ar—H); 7.46—7.73 (m, 2H, NH—Z+N$^6$H—CH$_2$); 8.10 (broad)+8.20 (2 s, 2H, C$^6$—H+C$^8$—H). MS (FAB): m/e=528.4 (100%; (M+H)$^+$).

17c) N$^6$-(3-(2S-(Benzyloxycarbonylamino)propionic acid))-N$^9$-(1-(4-aminobutyl))-adenine Synthesis analogously to Example 12c from N$^{6-3}$-(2S-(benzyloxycarbonylamino)propionic acid))-N$^9$-(1-(4-tert-butyloxycarbonyl-aminobutyl))-adenine (Example 17b). Yield: 100%.

$^1$H-NMR (200 MHz, DMSO): δ=1.48 (m, 2H, CH$_2$); 1.87 (m, 2H, CH$_2$); 2.80 (dt, 2H, CH$_2$—NH$_2$); 3.69–4.02 (m, 2H, CH$_2$—CH(NH—Z)); 4.20 (t, 2H, N$^9$—CH$_2$); 4.36 (m,1H, CH(NH—Z)); 5.01 (s, 2H, CH$_2$—Ph); 7.33 (s, 5H, Ar—H); 7.64 (s, broad, 4H, NH$_3^+$+N$^6$H—CH$_2$); 8.10 (broad)+8.20 (2 s, 2H, C$^6$—H+C$^8$—H). MS (ES+): m/e=428.3 (50%; (M+H)$^+$); 294.2 (100).

17d) N$^6$-(3-(2S-(Benzyloxycarbonylamino)propionic acid))-N$^9$-(1-(4-guanidinylbutyl))-adenine Synthesis analogously to Example 1d from N$^6$-(3-(2S-(benzyloxycarbonylamino)propionic acid))-N$^9$-(1-(4-aminobutyl))-adenine (Example 17c). Yield: 78%. MS (ES+): m/e=470.2 (50%; (M+H)$^+$); 336.2 (100).

Example 18

N$^6$-(3-(2S-(Benzyloxycarbonylamino)propionic acid))-N$^9$-(1-(4-(4,5-dihydro-1H-imidazol-2-yl) amino)butyl))-adenine Synthesis analogously to Example 4 from N$^6$-(3-(2S-(benzyloxycarbonylamino)propionic acid))-N$^9$-(1-(4- aminobutyl))-adenine (Example 17c). Yield: 41%. MS (ES+): m/e=496.3 (60%; (M+H)⁺); 362.2 (100).

Example 19

2S-Benzyloxycarbonylamino-3-(6-(4-(1,4,5,6-tetrahydropyrimidin-2-yl-carbamoyl)piperidin-1-yl)purin-9-yl)propionic acid 19a) tert-Butyl 2S-benzyloxycarbonylamino-3-(6-(4-carboxypiperidin-1-yl)purin-9-yl)-propionate 260 mg (0.6 mmol) of tert-butyl 2S-benzyloxycarbonylamino-3-(6-chloropurin-9-yl)-propionate (Example 1a), 116.3 mg (0.9 mmol) of piperidine-4-carboxylic acid and 310 mg (2.4 mmol) of DIPEA in 4 ml of absol. DMF were stirred at 60° C. for 16 h. A further 310 mg of DIPEA were then added and the mixture was again stirred at 60° C. for 24 h. The solvent was evaporated and the residue was partitioned between EA and water. The organic phase was washed again with $KHSO_4$/$K_2SO_4$ solution, then with NaCl solution, dried, filtered and concentrated. The residue was chromatographed through silica gel (EA). Yield: 219 mg (69%). MS (ES+): m/e=525.3 (100%; (M+H)⁺).

19b) tert-Butyl 2S-benzyloxycarbonylamino-3-(6-(4-(1,4,5,6-tetrahydropyrimidin-2-ylcarbamoyl)piperidin-1-yl)purin-9-yl)propionate 126 mg (0.24 mmol) of tert-butyl 2S-benzyloxycarbonylamino-3-(6-(4-carboxypiperidin-1-yl)purin-9-yl)propionate (Example 19a), 39.3 mg (0.29 mmol),of 2-amino-1,4,5,6-tetrahydropyrimidine hydrochloride, 86.6 mg (0.264 mmol) of TOTU (O-((ethoxycarbonyl)cyanomethylen-amino)-N,N,N',N'-tetramethyluronium tetrafluoroborate (W. König et al., Proceedings of the 21 st European Peptide Symposium 1990, E. Giralt, D. Andreu, Eds., ESCOM, Leiden, p. 143) and 124 mg of DIPEA were added successively to 3 ml of absol. DMF. The solution was stirred at RT for 3 h, then a further 28 mg of DIPEA were added and the solution was stirred at RT for 12 h. The reaction mixture was adjusted to pH 6 using glacial acetic acid/toluene (1:1), the reaction solution was concentrated, the residue was partitioned between EA and saturated $NaHCO_3$ solution, and the organic phase was washed with NaCl, dried and concentrated. The residue was chromatographed through silica gel (EA:MeOH:TEA 85:15:1.5). Yield: 70 mg. MS (ES+): m/e=606.4 (60%; (M+H)⁺); 416.3 (40); 275.7 (100).

19c) 2S-Benzyloxycarbonylamino-3-(6-(4-(1,4,5,6-tetrahydropyrimidin-2-yl-carbamoyl)piperidin-1-yl)purin-9-yl)propionic Acid 80 mg of tert-butyl 2S-benzyloxycarbonylamino-3-(6-(4-(1,4,5,6-tetrahydropyrimidin-2-ylcarbamoyl)piperidin-1-yl)purin-9-yl)propionate (Example 19b) were dissolved in 16 ml of precooled 95% strength trifluoroacetic acid and stirred first at 0° C. for 30 min, then at RT for 30 min. The trifluoroacetic acid was removed in a rotary evaporator, and the residue was coevaporated three times with toluene, stirred in ethanol/ether (1:2), washed with ether and dried in vacuo. Yield: 59 mg. MS (ES+): m/e=550.3 (60%; (M+H)⁺); 416.3 (100).

Example 20

2S-Benzyloxycarbonylamino-3-(1-(9-(2-guanidinoethyl)-9H-purin-6-yl)-1H-imidazol-4-yl)propionic Acid 20a) $N^9$-(1-(2-(tert-Butyloxycarbonylamino)ethyl))-6-chloropurine The synthesis was carried out analogously to Example 12a from 6-chloropurine and tert-butyl N-(2-tosyloxyethyl)carbamate. Yield: 36%.

¹H-NMR (200 MHz, DMSO): δ=1.24 (s, 9H, tBu); 3.40 (dt, 2H, $CH_2$—NHBoc); 4.35 (t, 2H, $N^9$—$CH_2$); 6.91 (t, broad, 1H, NH); 8.60+8.78 (2 s, 2H, C6—H+C8—H). MS (FAB): m/e=298.2 (100%; (M+H)⁺).

20b) 2S-Benzyloxycarbonylamino-3-(1-(9-(2-(tert-butyloxycarbonylamino)ethyl)-9H-purin6-yl)-1H-imidazol-4-yl)propionic Acid The synthesis was carried out analogously to Example 12b from $N^9$-(1-(2-(tert-butyloxycarbonylamino)ethyl))-6-chloropurine (Example 21a) and $N_\alpha$—Z—L-histidine. Yield: 33%. MS (ES+): m/e=551.3 (100%; (M+H)⁺).

20c) 3-(1-(9-(2-Aminoethyl)-9H-purin-6-yl)-1H-imidazol-4-yl)-2S-benzyloxycarbonylaminopropionic Acid The synthesis was carried out analogously to Example 12c from 2S-benzyloxycarbonylamino-3-(1-(9-(2-(tert-butyloxycarbonylamino)ethyl)-9H-purin-6-yl)-1H-imidazol-4-yl)propionic acid (Example 20b). Yield: 100%. MS (ES+): m/e=451.3 (70%; (M+H)⁺);

¹H-NMR (200 MHz, DMSO): δ=2.87–3.15 (m, 2H, Im—$CH_2$); 3.38–3.51 (m, 2H, $CH_2$—$NH_2$); 4.36 (m, 1H, CH—NHZ); 4.60 (t, 2H, $N^9$—$CH_2$); 5.00 (s, 2H, $CH_2$—Ph); 7.28 (s, 5H, aryl-H); 7.62 (d, 1H. NH—Z); 8.23+9.05 (2 s, 2H, ImH); 8.71+8.88 (2 s, 2H, C6—H+C8—H).

20d) 2S-Benzy(oxycarbonylamino-3-(1-(9-(2guanidinoethyl)-9H-purin-6-yl)-1H-imidazol4-yl)propionic acid The synthesis was carried out analogously to Example 1d from 3-(1-(9-(2-aminoethyl)-9H-purin-6-yl)-1H-imidazol4-yl)-2S-benzyloxycarbonylamino-propionic acid (Example 20c). Yield: 38%. MS (ES+): m/e 493.3 ((M+H)⁺);

Example 21

2R-Benzyloxycarbonylamino-3-(6-(N-(4-guanidinocyclohexyi)amino)purin-9-yl)propionic acid 21a) $N^9$-(3-(tert-butyl 2R-(Benzyloxycarbonylamino)propionate))-6-chloropurine The synthesis was carried out analogously to Example 1a from 6-chloropurine and N-benzyloxycarbonyl-D-serine tert-butyl ester. MS (FAB): m/e=432.2 (100%; (M+H)⁺); 376.1 (30).

21b) tert-Butyl 2R-benzyloxycarbonylamino-3-(6-( N-(4-(tert-butyloxycarbonylamino)cyclohexyl)amino)purin-9-yl)propionate The synthesis was carried out analogously to Example 1b from 4-amino-1-(tert-butyloxycarbonylamino)cyclohexane and $N^9$-(3-(tert-butyl 2R-(benzyloxycarbonylamino)propionate))chloropurine (Example 21a). Yield: 55%. MS (FAB): m/e=610.3 (100%; (M+H)⁺).

21c) 3-(6-(N-(4-Aminocyclohexyl)amino)purin-9-yl)-2R-benzyloxycarbonylaminopropionic Acid The synthesis was carried out analogously to Example 1c from tert-butyl 2R-benzyloxycarbonylamino-3-(6-(N-(4-(tert-butyloxycarbonylamino)-cyclohexyl)amino)purin-9-yl)propionate (Example 21b). Yield: 100%. MS (ES+): m/e=454.2 (50%, (M+H)⁺).

21d) 2R-Senzyloxycarbonylamino-3-(6-(N-(4guanidinocyclohexyl)amino)-purin-9-yl)propionic Acid The synthesis was carried out analogously to Example 1d from 3-(6-(N-(4-aminocyclohexyi)amino)purin-9-yl)-2R-benzyloxycarbonylaminopropionic acid (Example 21 c). Yield: 80%. MS (ES+): m/e=496.3 (50%, (M+H)⁺).

Example 22

2R-Benzyloxycarbonylamino-3-(6-(N-(3-guanidinomethylbenzyl)amino)-purin-9-yl)propionic Acid 22a) tert-Butyl 2R-benzyloxycarbonylamino-3-(6-(N-(3-tert-butyloxycarbonylaminomethylbenzyl)amino)purin-9-yl)propionate The synthesis was carried out analogously to Example 1b from 3-aminomethyl-1-(tert-butyloxycarbonylaminomethyl)benzene and $N^9$-(3-(tert-butyl 2R-(benzyloxycarbonylamino)propionate)-6-chloropurine (Example 21a). Yield: 51%. MS (ES+): m/e=632.3 (100%; (M+H)$^+$).

22b) 3-(6-(N-(3-Aminomethylbenzyl)amino)purin-9-yl)-2R-benzyloxycarbonylaminopropionic Acid The synthesis was carried out analogously to Example 1c from tert-butyl 2R-benzyloxycarbonylamino-3-(6-( N-(3-tert-butyloxycarbonyl-aminomethylbenzyl)amino)purin-9-yl)propionate (Example 22a). Yield: 100%. MS (ES+): m/e=476.2 ((M+H)$^+$, 50%); 342.2 (70).

22c) 2R-Benzyloxycarbonylamino-3-(6-(N-(3guanidinomethylbenzyl)amino)purin-9-yl)propionic Acid The synthesis was carried out analogously to Example 1d from 3-(6-(N-(3-aminomethylbenzyl)amino)purin-9-yl)-2R-benzyloxycarbonylamino-propionic acid (Example 22b). Yield: 30%. MS (ES+): m/e=518.3 ( (M+H)$^+$, 20%).

Example 23

3-(6-((4-(Benzimidazol-2-ylamino)butyl)amino)purin-9-yl)-2S-benzyloxycarbonylaminopropionic Acid 23a) 1-(4-tert-Butyloxycarbonylaminobutyl)-3-(2-nitrophenyl)thiourea 0.928 9 (5.15 mmol) of 2-nitrophenyl isothiocyanate in 5 ml of absol. DMF was added dropwise at 0° C. to 0.97 g (5.15 mmol) of 4-(tert-butyloxycarbonylaminobutyl)-1-amine in 25 ml of absol. DMF. The solvent was distilled off and the residue was chromatographed through silica gel (EA:n-heptane 1:2 to 1:1). Yield: 1.8 g (95%). MS (ES+): m/e=369.2 ( M+H)$^+$, 100%).

23b) 3-(2-Aminophenyl)-1-(4-tert-butyloxycarbonylaminobutyl)thiourea 1.78 g (4.8 mmol) of 1-(4-tert-butyloxycarbonylaminobutyl)-3-(2-nitrophenyl)thiourea (Example 23a) were dissolved in 120 ml of methanol and hydrogenated (1 bar) over 1 g of Pd/C at RT for 3 h. The catalyst was filtered off, the filtrate was concentrated and the residue was chromatographed through silica gel (EA:n-heptane 1:1). Yield: 1.4 g.

23c) 4-(Benzimidazol-2-ylamino)-1-(tert-butyloxycarbonylamino)butane 1.79 g (8.28 mmol) of yellow mercuric oxide and 27 mg of flowers of sulfur were added to 1.4 g (4.14 mmol) of 3-(2-aminophenyl)-1-(4-tert-butyloxycarbonylaminobutyl)thiourea (Example 23b) in 30 ml of ethanol and the reaction mixture was heated at 50–55° C. for 3 h. The solid was filtered off with suction and washed with ethanol. The filtrate was concentrated and the product was chromatographed through silica gel (DCM:methanol 9:5, then 9:1). Yield: 43%. MS (ES+): m/e=305.2 ( (M+H)$^+$, 100%).

23d) 4-(Benzimidazol-2-ylamino)-1-aminobutane 198 mg (0.65 mmol) of 4-(benzimidazol-2-ylamino)-1-(tert-butyloxycarbonylamino)butane (Example 23c) were dissolved in 20 ml of 95% strength trifluoroacetic acid at 0° C. and stirred at 0° C. for 2 h, then concentrated at RT during the course of 30 min. The residue was coevaporated three times with toluene, then stirred with ether and washed with pentane and dried in vacuo. Yield: 100%. MS (ES+): m/e=205.2 ( (M+H)$^+$, 100%).

23e) tert-Butyl 3-(6-((4-(benzimidazol-2-ylamino)butyl)amino)purin-9-yl)-2S-benzyloxycarbonylaminopropionate The synthesis was carried out analogously to Example 1b from 4-(benzimidazol-2-ylamino)-1-aminobutane (Example 23d) and $N^9$-(3-(tert-butyl 2S-(benzyloxycarbonylamino)propionate))-6chloropurine (Example 1a). Yield: 32%. MS (ES+): m/e=600.3 (100%; (M+H)$^+$).

23f) 3-(6-((4-(Benzimidazol-2-ylamino)butyl)amino)purin-9-yl)-2S-benzyloxycarbonylaminopropionic Acid The synthesis was carried out analogously to Example 1c from tert-butyl 3-(6-((4-(benzimidazol-2-ylamino)butyl)amino)purin-9-yl)-2S-benzyloxycarbonylaminopropionate (Example 23e). Yield: 100%. MS (ES+): m/e=544.2 ((M+H)$^+$, 70%).

Example 24

2S-Benzyloxycarbonylamino-3-(6-(4-((4,5-dihydro-1H-imidazol-2-ylamino)-methyl)piperidin-1-yl)purin-9-yl)propionic Acid 24a) tert-Butyl 3-(6-(4-(Aminomethyl)piperidin-1-yl)purin-9-yl)-2S-benzyloxycarbonylaminopropionate The synthesis was carried out analogously to Example 1 b from 4-(aminomethyl)piperidine and $N^9$-(3-(tert-butyl 2S-(benzyloxycarbonylamino)-propionate))-6-chloropurine (Example 1a). Yield: 96.4%. MS (ES+): m/e=510.3 (100%; (M+H)$^+$).

24b) 3-(6-(4-(Aminomethyl)piperidin-1-yl)purin-9-yl)-2S-benzyloxycarbonylaminopropionic Acid The synthesis was carried out analogously to Example 1c from tert-butyl 3-(6-(4-(aminomethyl)piperidin-1-yl)purin-9-yl)-2S-benzyloxycarbonylamino-propionate (Example 24a). Yield: 100%. MS (ES+): m/e=454.3 ((M+H)$^+$; 30%).

24c) 2S-Benzyloxycarbonylamino-3-(6-(4-((4,5-dihydro-1H-imidazol-2-yl-amino)methyl)piperidin-1-yl)purin-9-yl) propionic Acid The synthesis was carried out analogously to Example 4 from 3-(6-(4-(aminomethyl)piperidin-1-yl)purin-9-yl)-2S-benzyloxycarbonylamino-propionic acid (Example 24b). Yield: 95%. MS (ES+): m/e=522.3 ((M+H)$^+$, 40%).

Example 25

2R-Benzyloxycarbonylamino-3-(6-(4-((4,5-dihydro-1H-imidazol-2-ylamino)-methyl)piperidin-1-yl)purin-9-yl)propionic Acid The synthesis was carried out analogously to Example 24 from $N^9$-(3-(tert-butyl 2R-(benzyloxycarbonylamino)propionate))-6-chloropurine (Example 21a). MS (ES+): m/e=522.3 ((M+H)$^+$, 20%).

Example 26

2S-Benzyloxycarbonylamino-3-(6-(4-(guanidinomethyl)piperidin-1-yl)purin-9-yl)propionic Acid The synthesis was carried out analogously to Example 1d from 3-(6-(4-(aminomethyl)piperidin-1-yl)purin-9-yl)-2S-benzyloxycarbonylamino-propionic acid (Example 24b). Yield: 74%. MS (ES+): m/e=496.3 ((M+H)$^+$, 40%).

Example 27

2S-Benzyloxycarbonylamino-3-(6-(3-(3-benzyiureido)phenyisulfanyl)purin-9-yl)propionic Acid 27a) tert-Butyl 3-(6-(3-aminophenylsulfanyl)purin-9-yl)-2S-benzyloxycarbonylaminopropionate 0.602 mmol of 3-mercaptoaniline were stirred in DMF and DIPEA for 12 h together with 0.602 mmol of $N^9$-(3-(tert-butyl 2S-(benzyloxycarbonylamino)propionate))-6-chloropurine (Example 1a). The reaction solution was concentrated, the residue was partitioned between EA and saturated NaHCO₃ solution, the phases were separated, the organic phase was washed with half-saturated NaHCO₃ solution and NaCl solution, dried and concentrated, and the product was chromatographed through silica gel (EA:heptane 1:1). Yield: 190 mg. MS (ES+): m/e=521.3 ( (M+H)⁺, 100%).

27b) tert-Butyl 2S-benzyloxycarbonylamino-3-(6-(3-(3-benzylureido)phenylsulfanyl)purin-9-yl)propionate 46.1 mg of benzyl isocyanate in 1 ml of acetonitrile were added by means of a syringe to 180 mg of tert-butyl 3-(6-(3-aminophenylsulfanyl)purin-9-yl)-2S-benzyloxycarbonylaminopropionate (Example 27a) in 3 ml of absol, acetonitrile. The mixture was stirred at RT for 48 h and concentrated, and the residue was chromatographed through silica gel (DCM:EA 7:3 to 1:1). Yield: 205 mg. MS (ES+): m/e=654.4 ( (M+H)⁺, 100%).

27c) 2S-Benzyloxycarbonylamino-3-(6-(3-(3-benzylureido)-phenylsulfanyl)purin-9-yl)propionic Acid The synthesis was carried out analogously to Example 1c from tert-butyl 2S-benzyloxycarbonylamino-3-(6-(3-(3-benzylureido)phenyisulfanyl)purin-9-yl)propionate (Example 27b). Yield: 100%. MS (ES+): m/e 598.4 ((M+H)⁺, 100%).

Example 28

2S-Neopentyloxycarbonylamino-3-(6-(4-(1,4,5,6-tetrahydropyrimidin-2-yl-carbamoyl)piperidin-1-yl)purin-9-yl)propionic Acid 28a) tert-Butyl 2S-amino-3-(6-(4-carboxypiperidin-1-yl)purin-9-yl)-propionate 1.7 g of tert-butyl 2S-benzyloxycarbonylamino-3-(6-(4-carboxypiperidin-1-yl)purin-9-yl)propionate (Example 19a) were dissolved in 200 ml of AcOH and hydrogenated over Pd/C at an H₂ pressure of 1 atm. The catalyst was filtered off, the solvent was distilled off and the residue was lyophilized. Yield: 100%. MS (ES+): m/e=391.3 ((M+H)⁺, 100%).

28b) tert-Butyl 2S-neopentyloxycarbonylamino-3-(6-(4-carboxypiperidin-1-yl)purin-9-yl)propionate 390 mg (1 mmol) of tert-butyl 2S-amino-3-(6-(4-carboxypiperidin-1-yl)purin-9-yl)propionate (Example 20a) in 4 ml of DMF were treated at 0° C. with 230 mg (1 mmol) of N-(neopentyloxycarbonyloxy)succinimide and 0.17 ml of DIPEA and, after slowly warming, stirred at RT for 12 h. The reaction mixture was concentrated and the residue was chromatographed (Lobar-C, DCM:MeOH:AcOH:H₂O 90:10:1:1). Yield: 540 mg. MS (ES+): m/e=505.4 ((M+H)⁺, 100%).

28c) tert-Butyl 2S-neopentyloxycarbonylamino-3-(6-(4-(1,4,5,6-tetrahydropyrimidin-2-ylcarbamoyl)piperidin-1-yl)purin-9-yl)propionate 505 mg (1 mmol) of tert-butyl 2S-neopentyloxycarbonylamino-3-(6-(4-carboxypiperidin-1-yl)purin-9-yl)propionate (Example 20b) were dissolved in 10 ml of acetonitrile, treated with 250 mg of DCCl and 184 mg of pentafluorophenol and then stirred at RT for 30 minutes. The mixture was filtered, the mother liquor was concentrated, the residue was taken up in 5 ml of DMF, and the solution was treated with 200 mg of 2-amino-1,4,5,6-tetrahydropyrimidine and stirred at RT for 12 h. The solvent was distilled off in vacuo and the residue was chromatographed (Lobar-C, DCM:MeOH:AcOH:H₂O 98:8:0.8:0.8). Yield: 270 mg. MS (ES+): m/e=586.5 ((M+H)⁺, 100%).

28d) 2S-Neopentyloxycarbonylamino-3-(6-(4-(1,4,5,6-tetrahydropyrimidin-2-ylcarbamoyl)piperidin-1-yl)purin-9-yl)propionic Acid The synthesis was carried out analogously to Example 19c from tert-butyl 2S-neopentyloxycarbonylamino-3-(6-(4-(1,4,5,6-tetrahydropyrimidin-2-ylcarbamoyl)piperidin-1-yl)purin-9-yl)propionate (Example 28c). Yield: 94%. MS (ES+): m/e=530.4 ((M+H)⁺, 20%).

Example 29

2S-(1-Adamantylmethyloxycarbonylamino)-3-(6-(4-(1,4,5,6-tetrahydropyrimidin-2-ylcarbamoyl)piperidin-1-yl)purin-9-yl)propionic Acid 29a) tert-Butyl 2S-(1-adamantylmethyloxycarbonylamino)-3-(6-(4-carboxy-piperidin-1-yl)purin-9-yl)propionate The synthesis was carried out analogously to Example 28b from N-(1-adamantylmethyl-oxycarbonyloxy)succinimide and tert-butyl 2S-amino-3-(6-(4-carboxypiperidin-1-yl)purin-9-yl)propionate (Example 28a). Yield: 85%. MS (ES+): m/e=583.4 ((M+H)⁺, 100%).

29b) tert-Butyl 2S-(1-adamantylmethyloxycarbonylamino)-3-(6-(4-(1,4,5,6-tetrahydropyrimidin-2-ylcarbamoyl)piperidin-1-yl)purin-9-yl)propionate The synthesis was carried out analogously to Example 28c from tert-butyl 2S-(1-adamantylmethyloxycarbonylamino)-3-(6-(4-carboxypiperidin-1-yl)purin-9-yl)propionate (Example 29a). Yield: 75%. MS (ES+): m/e 664.5 ((M+H)⁺, 30%).

29c) 2S-(1-Adamantylmethyloxycarbonylamino)-3-(6-(4-(1,4,5,6-tetrahydropyrimidin-2-ylcarbamoyl)piperidin-1-yl)purin-9-yl)propionic Acid The synthesis was carried out analogously to Example 19c from tert-butyl 2S-(1-adamantylmethyloxycarbonylamino)-3-(6-(4-(1,4,5,6-tetrahydropyrimidin-2-yl-carbamoyl)piperidin-1-yl)purin-9-yl)propionate (Example 29b). Yield: 100%. MS (ES+): m/e 608.4 ((M+H)⁺, 10%).

Pharmacological Testing

The inhibition of binding of kistrin to human vitronectin receptor (VnR) is described below as a test method by which, for example, the antagonistic action of the compounds according to the invention on the vitronectin receptor $\alpha_v\beta_3$ can be determined ($\alpha_v\beta_3$ ELISA Test; the test method is abbreviated to "K/VnR" in the listing of the test results).

Purification of Kistrin

Kistrin is purified according to the methods of Dennis et al., as described in Proc. Natl. Acad. Sci. USA 1989, 87, 2471–2475 and PROTEINS: Structure, Function and Genetics 1993, 15, 312–321.

Purification of Human Vitronectin Receptor ($\alpha_v\beta_3$)

Human vitronectin receptor is obtained from the human placenta according to the method of Pytela et al., Methods Enzymol. 1987, 144, 475. Human vitronectin receptor $\alpha_v\beta_3$ can also be obtained from some cell lines (for example from 293 cells, a human embryonic kidney cell line), which are co-transfected with DNA sequences for both subunits $\alpha_v$ and $\beta_3$ of the vitronectin receptor. The subunits were extracted with octyl glycoside and then chromatographed through concanavalin A, heparin-Sepharose and S-300.

Monoclonal Antibodies

Murine monoclonal antibodies, specific for the $\beta_3$ subunits of the vitronectin receptor, are prepared according to the method of Newman et al., Blood, 1985, 227–232, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates are coated with a solution of kistrin (0.002 mg/ml) according to the method of Dennis et al., as described in PROTEINS: Structure, Function and Genetics 1993, 15, 312–321. The plates are then washed twice with PBS/0.05% Tween-20 and blocked by incubating (60 min) with bovine serum albumin (BSA, 0.5%, RIA grade or better) in Tris-HCl (50 mM), NaCl (100 mM), $MgCl_2$ (1 mM), $CaCl_2$ (1 mM), $MnCl_2$ (1 mM), pH 7. Solutions of known inhibitors and of the test substances are prepared in concentrations from $2\times10^{-12}$ to $2\times10^{-6}$ mol/l in assay buffer (BSA (0.5%, RIA grade or better) in Tris-HCl (50 mM), NaCl (100 mM), $MgCl_2$ (1 mM), $CaCl_2$ (1 mM), $MnCl_2$ (1 mM), pH 7). The blocked plates are emptied, and in each case 0.025 ml of this solution, which contains a defined concentration ($2\times10^{-12}$ to $2\times10^{-6}$ mol/l) either of a known inhibitor or of a test substance, are added to each well, 0.025 ml of a solution of the vitronectin receptor in the test buffer (0.03 mg/ml) is pipetted into each well of the plate and the plate is incubated at room temperature for 60–180 min on a shaker. In the meantime, a solution (6 ml/plate) of a murine monoclonal antibody specific for the $\beta_3$ subunit of the vitronectin receptor is prepared in the assay buffer (0.0015 mg/ml). A second rabbit antibody (0.001 ml of stock solution/6 ml of the murine monoclonal anti-$\beta_3$ antibody solution) which is an anti-mouse Fc HRP antibody conjugate is added to this solution, and this mixture of murine anti-$\beta_3$ antibody and rabbit anti-mouse Fc HRP antibody conjugate is incubated during the time of the receptor-inhibitor incubation. The test plates are washed four times with PBS solution which contains 0.05% Tween-20, and in each case 0.05 ml/well of the antibody mixture is pipetted into each well of the plate and incubated for 60–180 min. The plate is washed four times with PBS/0.05% Tween-20 and then developed with 0.05 ml/well of a PBS solution which contains 0.67 mg/ml of o-phenylenediamine and 0.012% of $H_2O_2$. Alternatively to this, o-phenylenediamine can be employed in a buffer (pH 5) which contains $Na_3PO_4$ and citric acid. The color development is stopped using 1 N $H_2SO_4$ (0.05 ml/well). The absorption for each well is measured at 492–405 nm and the data are evaluated by standard methods.

The following test results were obtained:

| Compound of Example | K/VnR Inhibition at 10 μM (in %) | K/VnR $IC_{50}$ (μM) |
| --- | --- | --- |
| 1 | 75 | 1.1 |
| 2 | 80 | 0.7 |
| 3 | 77 | 2.2 |
| 4 | 93 | 0.15 |
| 12 | 86 | 0.58 |
| 13 | 92 | 0.19 |
| 14 | 84 | 0.65 |
| 14c | 22 | |
| 15 | 92 | 0.21 |
| 16 | 85 | 0.54 |
| 16b | 29 | |
| 17 | 92 | 0.17 |
| 18 | 95 | 0.075 |
| 19 | 97 | 0.004 |
| 23 | 93 | 0.16 |
| 24 | 95 | 0.052 |
| 25 | 89 | 0.345 |
| 26 | 91 | 0.36 |

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 19653646.4, for which benefit under 35 USC §119 is claimed, is expressly incorporated herein in its entirety.

What is claimed is:

1. A compound of the formula I:

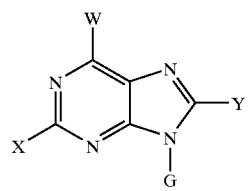

(I)

in which:

X is hydrogen;

Y is hydrogen;

G is a radical of the formula II

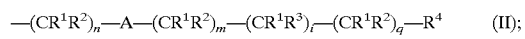

W is a radical of the formula III

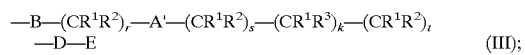

A, A' are a direct bond;

$R^1$, $R^2$ independently of one another are hydrogen or $(C_1–C_2)$-alkyl;

$R^3$ is $R^6R^{6'}N—R^7$, $R^6OC(O)N(R^5)R^7$, $R^6SO_2N(R^5)R^7$, $R^6C(O)N(R^5)R^7$, or $R^6N(R^{6'})C(O)N(R^5)R^7$;

$R^4$ is $C(O)R^8$;

$R^5$ is hydrogen or $(C_1–C_2)$-alkyl;

$R^6$, $R^{6'}$ independently of one another are hydrogen, $(C_1–C_{18})$-alkyl, $(C_3–C_{12})$-cycloalkyl, $(C_3–C_{12})$-cycloalkyl-$(C_1–C_8)$-alkyl, $(C_5–C_{14})$-aryl, in which 1 to 3 carbon atoms can be replaced by 1 to 3 heteroatoms selected from the group consisting of N, S, and O, or are $(C_5–C_{14})$-aryl-$(C_1–C_8)$-alkyl, in which 1 to 3 carbon atoms in aryl radicals can be replaced by 1 to 3 heteroatoms selected from the group consisting of N, S, and O, and where $R^6$ and $R^{6'}$, together with the atoms connecting them, can form a ring system which can optionally also contain additional heteroatoms selected from the group consisting of N, S, and O;

$R^7$ is a direct bond;

$R^8$ is hydroxyl, $(C_1–C_4)$-alkoxy, $(C_5–C_{14})$-aryl-$(C_1–C_4)$-alkoxy, $(C_5–C_{14})$-aryloxy, $(C_1–C_8)$-alkylcarbonyloxy $(C_1-C_4)$-alkoxy, or $(C_5-C_{14})$-aryl-$(C_1-C_4)$-alkylcarbonyloxy-$(C_1-C_4)$-alkoxy;

B is 1,4-piperidinediyl, where the nitrogen atom of the piperidine is bonded to the purine structure;

D is —$NR^6$— or —C(O)—$NR^6$—, where in the group —C(O)—$NR^6$— the nitrogen atom is bonded to the group E;

E is $R^6R^{6'}N$—C(=$NR^{6'}$)— or a radical selected from the group consisting of

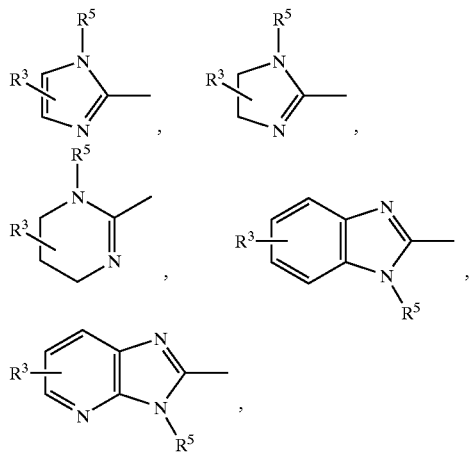

and which can optionally be monosubstituted, disubsitituted or trisubstituted by radicals selected from the group consisting of $R^3$, $R^5$, =O, =S, and $R^6R^{6'}N$—C(=$NR^6$)—;

r is zero or one;

s is zero;

t is zero;

k is zero;

n is one;

m is zero;

i is one;

q is zero;

in all its stereoisomeric forms and mixtures thereof in all ratios, and its physiologically tolerable salts.

2. A compound of the formula Ih

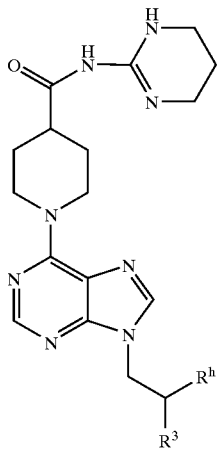

(Ih)

in which:

$R^3$ is $R^6R^6N$—$R^7$, $R^6OC(O)N(R^5)R^7$, $R^6SO_2N(R^5)R^7$, $R^6C(O)N(R^5)R^7$, or $R^6N(R^{6'})C(O)N(R^5)R^7$; and $R^h$ is $C(O)R^8$, where $R^5$, $R^6$, $R^{6'}$, $R^7$, and $R^8$ are as defined in claim 1; in all its stereoisometric forms and mixtures thereof in all ratios and its physiologically tolerable salts.

3. 2S-Benzyloxycarbonylamino-3-(6-(4-(1,4,5,6-tetrahydropyrimidin-2-yl-carbamoyl)piperidin-1-yl)purin-9-yl)propionic acid and its physiologically tolerable salts.

4. A method for inhibiting bone resorption by osteoclasts associated with inhibition of interactions between vitronectin receptors and their ligands comprising administering to a subject in need thereof an effective amount of at least one compound as claimed in claim 1.

5. A pharmaceutical preparation comprising at least one compound of the formula I as claimed in claim 1, and/or its physiologically tolerable salts, in addition to at least one pharmaceutically innocuous carrier, excipient, and/or additive.

6. A method for the treatment or prophylaxis of osteoporosis comprising administering to a subject in need thereof an effective amount of at least one compound of claim 1.

* * * * *